(12) United States Patent
Sanchez Barreiro et al.

(10) Patent No.: US 9,861,588 B2
(45) Date of Patent: Jan. 9, 2018

(54) NANOPARTICULATE SYSTEMS PREPARED FROM SORBITAN ESTERS

(71) Applicant: UNIVERSIDADE DE SANTIAGO DE COMPOSTELA, Santiago de Compostela (ES)

(72) Inventors: Alejandro Sanchez Barreiro, Santiago de Compostela (ES); Begoña Seijo Rey, Santiago de Compostela (ES); Giovanni Konat Zorzi, Santiago de Compostela (ES); Edison Luis Santana Carvalho, Santiago de Compostela (ES); Andrea Pensado Lopez, Santiago de Compostela (ES)

(73) Assignee: UNIVERSIDADE DE SANTIAGO DE COMPOSTELA, Santiago de Compostela (ES)

( * ) Notice: Subject to any disclaimer, the term of this patent is extended or adjusted under 35 U.S.C. 154(b) by 0 days.

(21) Appl. No.: 14/357,211

(22) PCT Filed: Nov. 8, 2012

(86) PCT No.: PCT/ES2012/070774
§ 371 (c)(1),
(2) Date: May 8, 2014

(87) PCT Pub. No.: WO2013/068625
PCT Pub. Date: May 16, 2013

(65) Prior Publication Data
US 2014/0314852 A1    Oct. 23, 2014

(30) Foreign Application Priority Data

Nov. 11, 2011 (ES) .................................. 201131812

(51) Int. Cl.
*A61K 9/51* (2006.01)
*A61K 8/02* (2006.01)
(Continued)

(52) U.S. Cl.
CPC .......... *A61K 9/5123* (2013.01); *A61K 8/0241* (2013.01); *A61K 8/4973* (2013.01);
(Continued)

(58) Field of Classification Search
None
See application file for complete search history.

(56) References Cited

U.S. PATENT DOCUMENTS 5,830,499 A   11/1998 Bouwstra
5,965,160 A   10/1999 Benita et al.
(Continued)

FOREIGN PATENT DOCUMENTS

EP    1961412 A1    8/2008

OTHER PUBLICATIONS

Abdelwahed et al., "Freeze-drying of nanopaorticles: Formulation, process and storage considerations", Adv. Drug Del. Rev., 58, pp. 1688-1713 (2006).*
(Continued)

*Primary Examiner* — Kevin S Orwig
*Assistant Examiner* — Barbara Frazier
(74) *Attorney, Agent, or Firm* — Hultquist, PLLC; Steven J. Hultquist

(57) ABSTRACT

The invention relates to systems comprising homogenous nanoparticles having an average size of less than 1 micrometer and containing at least a sorbitan ester, a macrogol ester, a macrogol ether or a derivative of same and, optionally, at least one component derived from oxyethylene and/or at least one component having an electric charge (positive or negative). According to the invention, the components are
(Continued)

incorporated in a single step consisting in mixing two solutions. The invention also relates to the use of said systems as medicines or medical devices, in tissue engineering or regenerative medicine, for cosmetic, hygienic or nutritional uses, and in surface coatings. The invention further relates to methods for preparing same.

22 Claims, 16 Drawing Sheets

(51) Int. Cl.
    A61K 8/49    (2006.01)
    A61K 8/60    (2006.01)
    A61K 8/73    (2006.01)
    A61K 8/86    (2006.01)
    A61K 9/14    (2006.01)
    A61K 39/00    (2006.01)
    A61K 47/18    (2017.01)
    A61K 47/26    (2006.01)
    A61Q 19/00    (2006.01)
    B82Y 5/00    (2011.01)
    C12N 15/113    (2010.01)
(52) U.S. Cl.
    CPC ............... *A61K 8/60* (2013.01); *A61K 8/735* (2013.01); *A61K 8/737* (2013.01); *A61K 8/86* (2013.01); *A61K 9/145* (2013.01); *A61K 9/51* (2013.01); *A61K 9/5192* (2013.01); *A61K 39/00* (2013.01); *A61K 47/18* (2013.01); *A61K 47/26* (2013.01); *A61Q 19/00* (2013.01); *C12N 15/113* (2013.01); *A61K 2800/10* (2013.01); *A61K 2800/412* (2013.01); *A61K 2800/56* (2013.01); *B82Y 5/00* (2013.01); *Y10T 428/2982* (2015.01)

(56) References Cited

U.S. PATENT DOCUMENTS

2010/0135938 A1* 6/2010 Ishikubo ................. A61K 8/062
    424/59
2010/0278975 A1* 11/2010 Chung ................. A61K 35/747
    426/61
2014/0343413 A1* 11/2014 Jolck .................. A61K 49/0457
    600/426

OTHER PUBLICATIONS

Sahoo et al., "Nanotechnology in ocular drug delivery", Drug Discovery Today, 13(3/4), pp. 144-151 (2008).*
Kim et al., "Oral Mucoadhesive Sustained Release Nanoparticle Coated Probiotic Nanofood", Tissue Engineering and Regenerative Medicine, 4(4), pp. 543-550 (2007).*
Bari, H., "A Prolonged Release Parenteral Drug Delivery System—An Overview", "International Journal of Pharmaceutical Sciences Review and Research", Jul.-Aug. 2010, pp. 1-11, vol. 3, No. 1.
Gref, R., et al., "Development and characterization of CyA-loaded poly(lactic acid)-poly(ethylene glycol)PEG micro-and nanoparticles. Comparison with conventional PLA particulate carriers", "European Journal of Pharmaceutics and Biopharmaceutics", 2001, pp. 111-118, vol. 51.
Kakkar, S., et al., "Spanlastics—A novel nanovesicular carrier system for ocular delivery", "International Journal of Pharmaceutics", Apr. 21, 2011, pp. 202-210, vol. 413.
Liu, H., et al., "Microemulsion with Sparaween as Mixed-surfactant and Synthesis of Iron Nanoparticles", "The Chinese Journal of Process Engineering", Feb. 2007, pp. 67-70 (English Abstract), vol. 7, No. 1.
Mueller, R., et al., "Solid lipid nanoparticles (SLN) for controlled drug delivery a review of the state of the art", "European Journal of Pharmaceutics and Biopharmaceutics", 2000, pp. 161-177, vol. 50.
Murdan, S., et al., "Interaction of a nonionic surfactant-based organogel with aqueous media", "International Journal of Pharmaceutics", 1999, pp. 211-214, vol. 180.
Murdan S., et al., "Novel gels and their dispersions—oral drug delivery systems for ciclosporin", "International Journal of Pharmaceutics", Jul. 11, 2005, pp. 113-124, vol. 300.
Murdan, S., et al., "Novel Sorbitan Monostearate Organogels", "Journal of Pharmaceutical Sciences", Apr. 21, 1999, pp. 608-614, vol. 88, No. 6.
Paolicelli, P. et al., "Surface-modified PLGA-based nanoparticles that can efficiently associate and deliver virus like particles", "Nanomedicine", Aug. 2010, pp. 843-853, vol. 5, No. 6.
Podczeck, F., et al., "The preparation of pellets containing non-ionic surfactants by extrusion/spheronization", "International Journal of Pharmaceutics", May 15, 2008, pp. 33-40, vol. 361.
Wissing, S., et al., "Solid lipid nanoparticles for parenteral drug delivery", "Advanced Drug Delivery Reviews", 2004, pp. 1257-1272, vol. 56.
Note: For the non-patent literature citations that no month of publication is indicted, the year of publication is more than 1 year prior to the effective filing date of the present application.
Balakrishnan, P., et al., "Formulation and in vitro assessment of minoxidil niosomes for enhanced skin delivery", "International Journal of Pharmaceutics", Apr. 24, 2009, pp. 1-8, vol. 377.
Lee, H., et al., "Target-specific intracellular delivery of siRNA using degradable hyaluronic acid nanogels", "Journal of Controlled Release", Feb. 27, 2007, pp. 245-252, vol. 119.
Mayer, M., et al., "Characterization of Ligand Binding by Saturation Transfer Difference NMR Spectroscopy", "Angewandte Chemie International Edition", Jan. 8, 1999, pp. 1784-1788, vol. 38, No. 12.
Novoa-Carballal, R., et al., "Disclosing an NMR-Invisible Fraction in Chitosan and PEGylated Copolymers and Its Role on the Determination of Degrees of Substitution", "Molecular Pharmaceutics", Jul. 3, 2013, pp. 3225-3231, vol. 10.
Pensado, A., et al., "Structual Analysis of Nanosystems: Solid Sorbitan esters Nanoparticles (SSN) as a Case Study", "European Journal of Pharmaceutics and Biopharmaceutics", May 6, 2016, pp. 189-199, vol. 104.

* cited by examiner

NANOPARTICULATE SYSTEMS PREPARED FROM SORBITAN ESTERS

CROSS-REFERENCE TO RELATED APPLICATIONS

This application is a U.S. national phase under the provisions of 35 U.S.C. §371 of International Patent Application No. PCT/ES12/70774 filed Nov. 8, 2012, which in turn claims priority of Spanish Patent Application No. P201131812 filed Nov. 11, 2011. The disclosures of such international patent application and Spanish priority patent application are hereby incorporated herein by reference in their respective entireties, for all purposes.

FIELD OF THE INVENTION

The present invention relates to systems comprising nanoparticles capable of encapsulating substances. More specifically, it relates to nanoparticulate systems comprising sorbitan esters. The present invention also relates to a method of preparing these systems and to their applications in the field of medicine.

BACKGROUND OF THE INVENTION

Micelles, mixed micelles, emulsions, micro- and nanoparticles and liposomes, which can consist of different types of raw materials and can be obtained by means of a very wide range of preparation techniques, stand out among colloidal systems proposed for active ingredient transport described in the literature. In any case, the raw materials used in preparing drug release systems will be selected depending on the preferred route of administration and taking into account their approval by the competent authorities.

One material that is common to some of these pharmaceutical carriers are the surface-active substances frequently involved in the processes of preparing same and are incorporated in small amounts.

Only in some cases could surfactants be used as fundamental ingredients of said pharmaceutical carriers. Sorbitan esters are one of these surfactants, and they are of great interest due to their biocompatibility. Sorbitan esters are frequently used in the pharmaceutical industry. The use thereof is due to their properties as lipophilic non-ionic surfactants. Precisely because of this, a person skilled in the art knows that said properties manifest at low surface-active agent concentrations (Owen I. Corrigan and Anne Marie Healy, Surfactants in Pharmaceutical Products and Systems, Encyclopedia of Pharmaceutical Technology, Vol. 14 (Swarbrick, J. and Boylan, J. C., Ed.). Specifically, sorbitan ester concentrations not exceeding 15% are described in the literature (Handbook of Pharmaceutical Excipients, Sixth Edition, Rowe, R. C., Sheskey, P. J. and Weller, P. J (Ed.), Pharmaceutical Press, Chicago, 2009).

In the described context it must be mentioned that there have been authors who have used sorbitan esters as the main component in systems they have developed despite referring to said sorbitan esters as surfactants. The development of millimetric pellet-type systems or of macroscopic gel-type systems, specifically referred to as organogels, for example, could be cited.

In the first case, it is described that the maximum concentration used to obtain pellet-type systems was comprised between 50% for sorbitan monostearate (span 60) and 80% for sorbitan monooleate (span 80) (Podczeck, F., Alessi, P. and Newton, J. M., Int. J. Pharm., 361, 2008, 33-40). Nevertheless, the mentioned authors found that far from developing systems consisting exclusively of said components, the maximum amount of sorbitan ester that could be incorporated into the final systems does not even amount to 23%.

In the second case, macroscopic gels are obtained using high percentages of sorbitan esters (Bari, H., International Journal of Pharmaceutical Sciences Review and Research, Volume 3, Issue 1, July-August 2010; Article 001), (Murdan, Gregoriadis and Florence, International Journal of Pharmaceutics 180 (1999) 211-214) (Murdan, Gregoriadis and Florence, J Pharm Sci., Vol. 88, No. 6, June 1999).

Based on the foregoing, when considering the use of sorbitan esters and referring to them as a surfactant, the person skilled in the art does not consider using them in a high proportion because said proportion would not enable their properties as a surfactant. However, even if the person skilled in the art intends to consider it as a single component or even a majority component of a formulation, it can be inferred from what is described in the literature that only systems having a size greater than micrometers can be developed with such component.

The only systems that could be developed up until now using sorbitan esters as the main component are the following:

A) Microparticulate systems with a mean diameter greater than one micrometer;

B) Microemulsions (LIU Hai-shui, LI Tie-long, JIN Zhao-hui, GONG Yan-zhang, ZHANG Yun-xia, Microemulsion with Span®/Tween as Mixed-surfactant and Synthesis of Iron Nanoparticles, The Chinese Journal of Process Engineering, DOI CNKI-ISSN: 1009-606X.0.2007-01-013) (EP1961412A1);

C) Vesicular reservoir-type nanosystems (e.g. liposomes or niosomes or nanocapsules) as in the case of nanovesicular systems described by Shilpa Kakkar, Indu Pal Kaur in the International Journal of Pharmaceutics, doi:10.1016/j.ijpharm.2011.04.027.

Liposomes are colloidal vesicles in which a bilayer membrane structure made up of different types of lipids encloses or encapsulates part of the aqueous phase in which the liposomes themselves are dispersed. The basic unit of the liposomes structure is, therefore, the lipid bilayer forming the vesicular membrane, the formation of which takes place spontaneously in the presence of water. Levels of sophistication in the structure and production method thereof have been incorporated to this spontaneous formation, thus improving the capacity thereof to act like drug release systems and, to the same extent, the possible therapeutic applications thereof. The lipid composition, the particle or vesicle size, the number of lamellae or bilayers forming the wall, as well as the composition of the internal and external aqueous phases or the method of preparation, determine the physicochemical characteristics of the vesicles, their drug encapsulation capacity, and also their stability and behavior both in vivo and in vitro. Liposomes are considered drug carrier systems. However, despite enormous interest, there are significant problems, particularly relating to system stability in body fluids and, particularly, in the bloodstream, where excessive drug loss and rapid interception of the system occurs, with the subsequent removal thereof from circulation, by mononuclear phagocyte system (MPS) cells (Andresen et al., Progress in Lipid Research 44 (2005) 68-97). Such finding represents an obstacle for liposomes as drug carrier systems. It was further found that liposomes generally have a limited encapsulation capacity, especially with respect to hydrophilic drugs, as well as a heterogeneous size, a lack of reproducibility of the prepared formulations often being observed, those characteristics also being related to the methods of preparation thereof (Lian and Ho, JOURNAL OF PHARMACEUTICAL SCIENCES, VOL. 90, NO. 6, JUNE 2001, 667-680).

The three types of systems mentioned above have a serious problem concerning stability. Vesicular systems and emulsions are known to experience aggregation phenomena, and the difficulty in obtaining more stable formulations by means of processes such as lyophilization without significantly changing their initial characteristics is also known. In this sense, it is important to bear in mind that a considerable energy input and/or the use of specific combinations of surface-active agents is necessary for the formation of such systems, so the obtained product is in an energetically unfavorable situation or unstable. Furthermore, these systems are particularly sensitive to variations in the surrounding area, such as temperature.

On the other hand, microparticulate systems have a certain tendency for sedimentation due to the influence of gravitational force.

As the nanoparticles are matrix-type nanosystems, they are suitable drug release systems because they are more stable than those mentioned above, generally have a greater encapsulation capacity; they can be prepared with a homogenous size.

However, it is not possible to prepare nanoparticles based on sorbitan esters following the teaching of the state of the art, considering nanoparticles consisting of lipophilic components such as solid lipid nanoparticles (SLN) as the closest state of the art (Rainer H. Müller, Karsten Mäder, Sven Gohla, European Journal of Pharmaceutics and Biopharmaceutics 50 (2000) 161-177), (S. A. Wissing, O. Kayser, R. H. Advanced Drug Delivery Reviews 56 (2004) 1257-1272).

One of the methods for preparing nanoparticles using excipients having low water-solubility, such as polyesters, is known as emulsification-evaporation, described for example in the scientific article by Gref et al., European Journal of Pharmaceutics and Biopharmaceutics, 51, 2001, 111-118. When the method described in section 2.2 on page 112 is followed, using sorbitan esters as the only component in the organic phase, nanoparticles are not obtained but an aggregate is (see Example 1A of the present specification).

Also, when trying to use another technique such as nanoprecipitation (Paolicelli et al., Nanomedicine, 5, 2010, 843-853), which is frequent in lipid nanoparticle development, it can again be confirmed that a technique with which it is possible to readily obtain nanoparticles based on components having low water-solubility is inefficient for developing nanoparticles with any percentage content by mass of a sorbitan ester (see Example 1B of the present specification).

DESCRIPTION OF THE INVENTION

The authors of the present invention have developed nanoparticles primarily consisting of sorbitan esters, which are stable and suitable for drug release. Sorbitan esters are used in the present invention not as a surfactant recognized for its safety, or established by the FDA and the pharmaceutical industry as, "generally recognized as safe" (GRAS), intended for enabling the production of a dosage form, but rather only as a GRAS lipophilic material forming same. In fact, the present invention provides nanoparticles consisting exclusively of sorbitan esters, which are therefore a basic component, unlike the teachings of the state of the art in which sorbitan esters are used as an excipient facilitating the production of nanoparticles consisting for the most part of other components.

The incorporation of various additional components is also possible. These additional components allow modulating system characteristics, making the system very versatile in terms of physicochemical characteristics and the interaction with other components, and they facilitate incorporating both lipophilic and hydrophilic active ingredients.

The internal structure of the drug release system of the present invention is not an aqueous inner space surrounded by a lipid bilayer nor it is based on nanoemulsions, but rather it is a homogenous nanoparticulate matrix structure.

The invention furthermore provides a method of preparation of said nanoparticulate system characterized by the spontaneous formation occurring in a single step by means of a simple technique that does not require the use of injection or homogenization, wherein the nanoparticles forming said nanoparticulate system comprise at least one sorbitan ester as the main component of the nanoparticles. The solvents used are not toxic, and furthermore the conditions in which the system of the present invention is prepared are mild, such that it is possible to incorporate genetic material or proteins without risking degradation and/or loss of biological activity.

One advantage associated with the system of the invention is that it is suitable as a promoter for promoting skin and mucous membrane surface penetration and as a promoter for promoting the absorption of different active ingredients.

Therefore, in one aspect the invention relates to nanoparticles comprising a sorbitan ester in a proportion by weight of between 60% and 100%.

Additionally, the nanoparticle of the invention can also optionally comprise other components, such as a cationic substance, an anionic substance, an ethylene oxide derivative, or combinations thereof, for example.

Additionally, the nanoparticle of the invention can also comprise an active ingredient.

Additionally, the nanoparticle of the invention can comprise a compound selected from a marker, an adjuvant, an immunomodulator, an antibody, an aptamer, a surface receptor, a stabilizing compound, a compound sensitive to chemical polymerization or combinations thereof.

In another aspect, the invention relates to a pharmaceutical composition comprising the previously described nanoparticles and a pharmaceutically acceptable carrier.

In another aspect, the invention relates to a cosmetic composition comprising the previously described nanoparticles.

In another aspect, the invention relates to a nutritional composition comprising the previously described nanoparticles.

In another aspect, the invention relates to a medical device comprising the previously described nanoparticles.

In another aspect, the invention relates to a surface coating substance comprising the previously described nanoparticles.

In another aspect, the invention relates to the use of the previously described nanoparticles in the preparation of a medicinal product. Said medicinal product can be used together with other medicinal products in combined therapies. Therefore, in a particular embodiment the invention relates to the use of the previously described nanoparticles for preparing a medicinal product for combined therapy.

In another aspect, the present invention relates to a method for the preparation of the previously described nanoparticles, comprising the following steps:
a) preparing an organic phase comprising a sorbitan ester in a proportion by weight of between 60% and 100%;
b) mixing under stirring the solution obtained in a) with an aqueous solution.

A final aspect of the invention relates to nanoparticles obtainable as previously described.

DETAILED DESCRIPTION OF THE INVENTION

Figure 1:
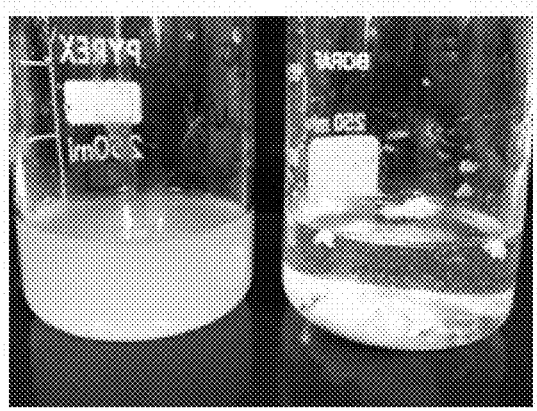
FIG. 1. Photograph of the nanoparticles prepared using PLGA:sorbitan ester at a ratio of 39:1 (left) and of the aggregate obtained when sorbitan ester is used exclusively (right), as described in Example 1.
Figure 2:
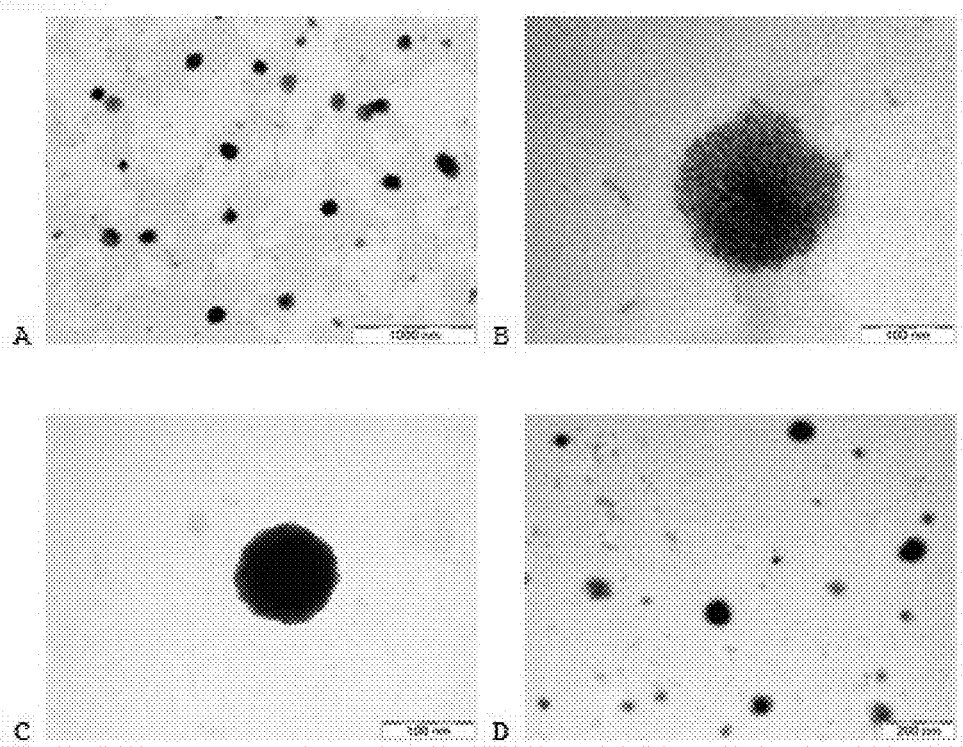
FIG. 2. Morphology of the nanoparticles prepared with Span® 80 and OA (A and B), Span® 80 and CTAB (C) or Span® 80 and BZC (D), observed by means of transmission electron microscopy at different magnifications.

The invention relates to nanoparticles, as previously described, suitable for encapsulating substances, for example, active ingredients or markers.

Depending on the components used and the method of preparation selected, these nanoparticles allow the vehiculization of different types of active substances, from hydrophilic molecules to very hydrophobic drugs. The substance encapsulated in the nanoparticles is dissolved, trapped and/or adsorbed in the colloidal structure.

In the present invention, the term "nanoparticles" is interpreted to mean that they are solid colloidal materials, the mean size of which ranges between 1 and 999 nm, having a solid matrix structure; they are further characterized by being stable structures having perfectly homogenous, reproducible and modulable characteristics.

The nanoparticles of the systems of the invention are perfectly distinguishable from other colloidal systems due to their structural characteristics; for example, the nanoparticles of the invention do not have lipid bilayers characteristics of liposomes; nor do they have an oily core characteristic of nanoemulsions or nanocapsules. The nanoparticles of the invention do not comprise oils or oily components.

In a particular embodiment, the invention relates to nanoparticles comprising a sorbitan ester in a proportion by weight of between 60% and 100%, characterized by being a solid homogenous matrix, the mean size of which is comprised between 1 and 999 nm. In a particular embodiment, the nanoparticles comprise a sorbitan ester in a proportion by weight of between 80% and 100%. More preferably, the nanoparticles of the invention comprise a sorbitan ester in a proportion by weight of between 90% and 100%. In a particular embodiment, the nanoparticles of the invention are further characterized by not comprising oils or oily components.

The nanoparticles of the system of the invention have an average particle size of between 1 and 999 nm, preferably between 50 and 600 nm, even more preferably between 100 and 400 nm. The average particle size is primarily influenced by the composition and the conditions for forming the particles established in the selected production method.

The term "average size" is interpreted to mean the average diameter of the population of nanoparticles moving together in an aqueous medium. The average size of these systems can be measured using standard methods known to the person skilled in the art and described in the experimental part below.

The population of nanoparticles of the invention moving together in an aqueous medium has a polydispersity index of less than 0.2, more preferably between 0 and 0.1 This means that the particles comprised in the system have a homogenous size distribution.

The nanoparticles of the systems of the invention have a matrix structure that allows incorporating additional components increasing and improving their stability, such as anionic and/or cationic polymers and modifications with ethylene oxide, for example. In a particular embodiment of the invention, the nanoparticles additionally comprise a cationic substance, an anionic substance, an ethylene oxide derivative, or combinations thereof, in a proportion by weight between 0% and 40% with respect to the total weight of the nanoparticle components. In a particular embodiment, the proportion by weight of the cationic substance, anionic substance, ethylene oxide derivative or the combination thereof, is comprised between 0% and 20% with respect to the total weight of the nanoparticle components; more particularly between 0% and 10%.

In addition, the nanoparticles have an electric charge (measured by means of Z potential), the magnitude of which can be modulated by means of a suitable system composition selection. Specifically, said electric charge can have positive or negative values depending on the system components and the proportion existing between them. The zeta potential of the nanoparticles of the systems of the invention can be measured using standard methods known to the person skilled in the art and described, for example, in the experimental part of the present specification.

In a particular embodiment of the invention, the nanoparticles have a charge ranging between −50 mV and +60 mV, even more preferably between −40 mV and +50 mV, depending on the proportion of the components.

In addition, the possibility offered by the present invention of modulating the electric charge of nanoparticles has enormous advantages. In that sense, a negative charge is particularly suitable for assuring nanoparticle stability after parenteral administration. In a particular embodiment, the invention relates to the previously described nanoparticles characterized by having a charge comprised between −50 mV and −20 mV.

Furthermore, the positive charge is particularly suitable for improving interaction with mucous membranes (which are generally negatively charged). It is possible to modulate the charge of the nanoparticles of the invention so that they are positively charged, for example and without being limited to these cases, when they further comprise a cationic substance in a proportion by weight not exceeding 40% in relation to the total weight of the system components. Therefore, in a particular embodiment the invention relates to the previously described nanoparticles characterized by having a charge comprised between +55 mV and +20 mV.

System Components

Sorbitan Esters

Sorbitan consists of a mixture of cyclic anhydrides of sorbitol, such as for example and without being limited to, 1,4-anhydrosorbitol, 1,5-anhydrosorbitol and 1,4,3,6-dianhydrosorbitol.

"Sorbitan esters" are interpreted to mean esterified sorbitan derivatives where the ester groups have a substituent selected from alkyl, alkenyl and alkynyl. Sorbitan esters include derivatives in which one, two, three or four hydroxyl groups are esterified, and they even include esterified derivatives in which one ester molecule is present for every two sorbitan molecules (in which case they are referred to with the "sesqui-" prefix). In that sense, for example, sorbitan monooleate is the sorbitan ester resulting from esterifying a hydroxyl group with oleic acid; sorbitan trioleate is the sorbitan ester resulting from esterifying three sorbitan hydroxyl groups with oleic acid.

"Alkyl" is interpreted to mean a linear or branched hydrocarbon chain that contains no instauration, of 1 to 24 carbon atoms, optionally substituted with one to three substituents selected from —$OR^b$, —$SR^b$, —$NR^aR^b$, —$C(O)R^b$, —$CO_2R^b$, —$C(O)NR^aR^b$, —$NR^aC(O)R^b$, —$NR^aC(O)OR^b$, —$NR^aC(O)NR^aR^b$, —$CF_3$, —$OCF_3$; where $R^a$ and $R^b$ are independently selected from hydrogen, alkyl, alkenyl and alkynyl.

"Alkenyl" and "alkynyl" in the compounds of the present invention refer to a linear or branched hydrocarbon chain containing at least one instauration, of 2 to 24 carbon atoms, optionally substituted with one to three substituents selected from —$OR^b$, —$SR^b$, —$NR^aR^b$, —$C(O)R^b$, —$CO_2R^b$, —$C(O)NR^aR^b$, —$NR^aC(O)R^b$, —$NR^aC(O)OR^b$, —$NR^aC(O)NR^aR^b$, —$CF_3$, —$OCF_3$; where $R^a$ and $R^b$ are as previously defined.

In a preferred embodiment, alkyl, alkenyl and alkynyl have a chain of between 6 and 24 carbon atoms, more preferably between 10 and 16 carbon atoms.

In a particular embodiment, sorbitan ester is selected from the group consisting of sorbitan mono-, di-, tri- or sesquioleate; sorbitan mono-, di-, tri- or sesquilaurate; sorbitan mono-, di-, tri- or sesquipalmitate; sorbitan mono-, di-, trior sesquistearate; and sorbitan mono-, di-, tri- or sesqui-isostearate; and their combinations.

Sorbitan esters are non-ionic surfactants given that they contain two localized regions, a hydrophilic region and another hydrophobic region. These non-ionic surfactants have the advantage of being less irritating than anionic or cationic surfactants. Furthermore, they are generally compatible with both anionic and cationic substances, since they are not ionized in solution.

Optional Components

In a particular embodiment, the systems of the invention further comprise a cationic substance.

The cationic substance allows modulating the characteristics of nanoparticulate systems, such as particle size, electrical surface charge and composition, for example, and thus making them more versatile.

In the context of the present invention, "cationic substance" is interpreted to mean that molecule provided with a positive electric charge, for example ammonium salts, cationic polymers and lipophilic or fatty amines.

In a particular embodiment, the cationic polymer is selected from protamine, polyglutamic acid, cationized dextran, polyamino acids and cationized proteins, and their salts.

The term "cationized" refers to the presence of a positively charged group which may be present naturally or may be introduced by means of a chemical reaction.

In a particular embodiment, the polyamino acids are selected from polylysine and polyarginine. In another particular embodiment, the cationized proteins are selected from gelatin, albumin, collagen and atelocollagen, and their cationized derivatives.

In a particular embodiment, the ammonium salts are selected from cetyltrimethylammonium bromide and benzalkonium chloride. In another particular embodiment, the fatty amine is oleylamine (cis-1-amino-9-octadecene).

In a particular embodiment, the systems of the invention can further comprise an anionic substance. The anionic substance is preferably an anionic polymer.

The term "anionic polymer" is interpreted to mean any polymer with a negative net charge, said definition including those anionic polymers to which modifications such as enzymatic or chemical fragmentation or derivatization were made.

The anionic polymer is selected from the group consisting of hyaluronic acid, colominic acid, polysialic acid, chondroitin, keratan, dextrans, heparin, carrageenans, furcellarans, alginates, agar-agar, glucomannan, gellan gum, locust bean gum, guar gum, tragacanth gum, acacia gum, xanthan gum, karaya gum, pectins, celluloses, starches, their salts, fragments, derivatives or combinations thereof.

Hyaluronan is a linear polymer comprising the repetition of a disaccharide structure formed by the alternating addition of acid D-glucuronic and D-N-acetylglucosamine, bound by alternating beta-1,4 and beta-1,3 glycosidic bonds as shown in the following formula:

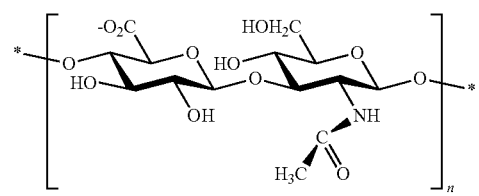

in which the integer n represents the degree of polymerization, i.e., the number of disaccharide units in the hyaluronan chain.

In the context of the present invention, hyaluronic acid with a broad range of molecular weights can be used. High molecular weight hyaluronic acid of is commercially available, whereas hyaluronic acid having a lower molecular weight can be obtained by means of high molecular weight hyaluronic acid fragmentation, using, for example, a hyaluronidase enzyme.

The term "hyaluronic acid, hyaluronan" as it is used herein includes either hyaluronic acid or a conjugate base thereof (hyaluronate). This conjugate base can be an alkaline salt of hyaluronic acid, including inorganic salts such as, for example, sodium, potassium, calcium, ammonium, magnesium, aluminum and lithium salts, organic salts such as basic amino acid salts at neutral pH, said salts are preferably pharmaceutically acceptable. In a preferred embodiment of the invention, the alkaline salt is hyaluronic acid sodium salt.

The family of polysialic acids, a term including colominic acid, is made up of linear polymers consisting of N-acetylneuraminic acid (Neu5Ac; also known as sialic acid) residues, N-acetylneuraminic acid being a natural constituent of cells and tissues, bound by $\alpha\text{-}(2\rightarrow 8)$ glycosidic bonds. Each N-acetylneuraminic acid residue has a carboxyl group, which is responsible for the negative charge of colominic acid, as shown in the following formula:

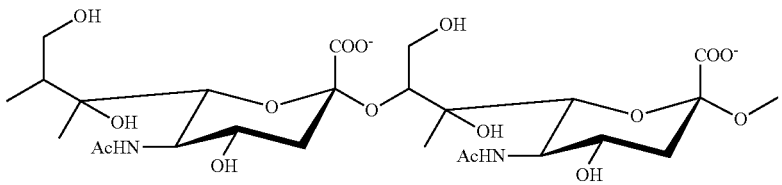

It is a material of unquestionable interest in the pharmaceutical and cosmetic field as it is biocompatible, biodegradable and non-immunogenic, the degradation products of which are not toxic (Gregoriadis G et al. Cell. Mol. Life Sci. 2000, 57, 1964-1969). In addition, polysialic acids are characterized by having, among other properties, a very long plasma half-life, so they were proposed as an alternative to polyethylene glycol derivatives to prolong the plasma residence time of drugs and active ingredient release systems, such as liposomes. In fact, patent "WO/2008/033253—Liposome complexes containing pharmaceutical agents and methods" uses them to make surface modifications to preformed liposomes. Finally, taking into account its structural characteristics, this material offers the possibility of modification, for example of introducing amino groups and the subsequent cationization.

Dextran sulfate is a complex glucan (polysaccharide) consisting of glucose molecule units, each of which contains about two sulfate groups as shown in the following formula:

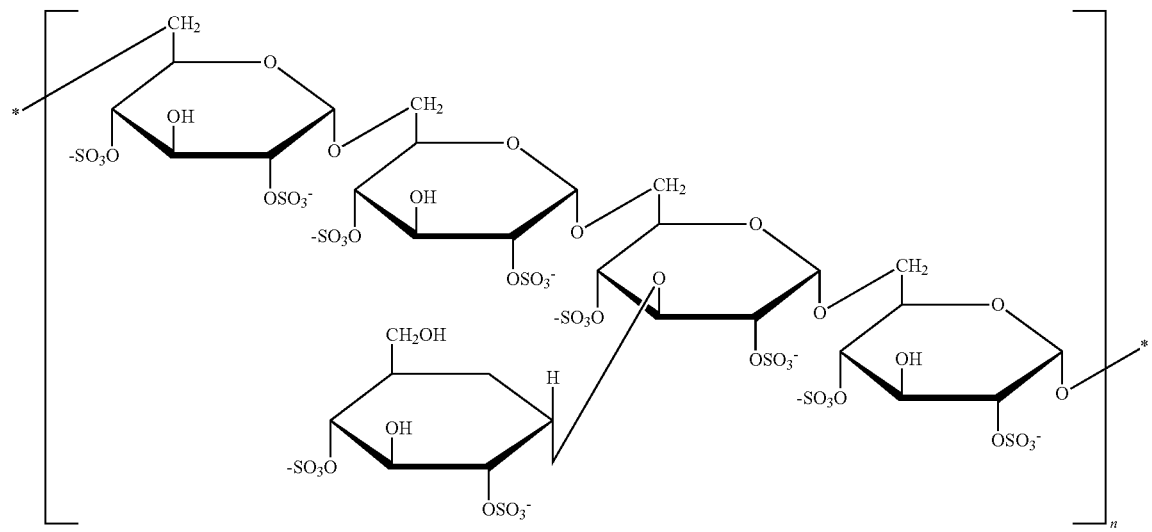

Dextran sulfate is prepared by means of dextran sulfation and subsequent purification by means of methods that are well-known to a person skilled in the art.

Heparin is a substance of natural origin from the family of glycosaminoglycans the chemical structure of which comprises the repetition of disaccharide monomer units of 2-O-sulfo-α-L-iduronic acid and 2-deoxy-2-sulfamide-α-D-glucopyranosyl-6-O-sulfate, depicted below:

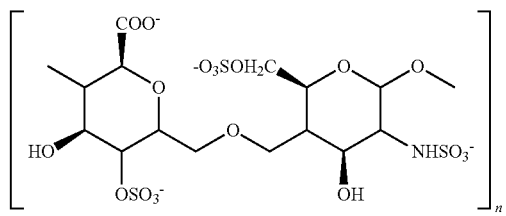

where n is an integer and represents the degree of polymerization, i.e., the number of monomer units in the heparin chain.

In the context of the present invention, it is possible to use both fractionated heparin and non-fractionated heparin. Conventional heparin or non-fractionated heparin is clearly distinguished from fractionated or low molecular weight heparin. The first one is a natural substance present in all vertebrates. Both types of heparin can be used in the form of a free base or in the form of a salt, such as sodium or calcium salt thereof, for example.

Fractionated or low molecular weight heparin is produced by the chemical or enzymatic depolymerization of conventional heparins. Examples of such heparins are enoxaparin, parnaparin, dalteparin and nadroparin, as well as their salts, such as sodium and calcium salts.

Heparin derivatives can also be used in the composition of the nanoparticulate systems of the present invention. These derivatives are known in the state of the art and originate as a result of the reactivity of the different functional groups present in the molecule. In that sense, oxidized or reduced N-acetylated, O-decarboxylated heparins are widely known.

Chondroitin sulfate is sulfated glycosaminoglycan (GAG) made up of a chain of alternating sugars. It is normally bound to proteins as part of a proteoglycan. It is depicted by means of the following structure:

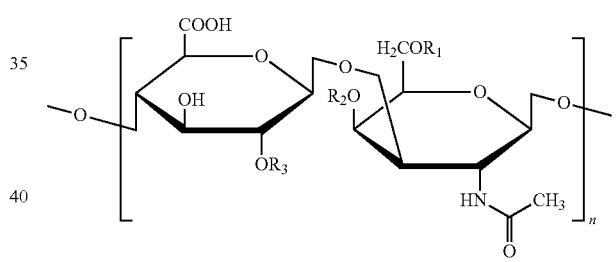

wherein n is an integer and represents the degree of polymerization, i.e., the number of disaccharide units in the chondroitin sulfate chain, and wherein $R_1$, $R_2$ and $R_3$ are independently hydrogen or an $SO_3H$ group. Each monosaccharide can be left without being sulfated, be sulfated once or be sulfated twice. Sulfation is mediated by specific sulfotransferases.

In the context of the present invention, the term "chondroitin sulfate" includes all its different isomers and derivatives, as well as combinations thereof.

In a particular embodiment, chondroitin sulfate is selected from the following substances and combinations thereof:
 chondroitin sulfate A, which is predominantly sulfated in the carbon 4 position of the N-acetylgalactosamine (GalNAc) sugar and is also known as 4-chondroitin sulfate ($R_1$=H, $R_2$=$SO_3H$ and $R_3$=H)
 chondroitin sulfate B, which is also referred to as dermatan sulfate. This substance is made up of units of linear repetition containing N-acetylgalactosamine and either L-iduronic acid or glucuronic acid, and each disaccharide can be sulfated once or be sulfated twice. It is mostly present in the skin, but it is also found in blood vessels, heart valves, tendons and the lungs.

chondroitin sulfate C, which is predominantly sulfated in the carbon 6 position of the GalNAc sugar and is also known as 6-chondroitin sulfate ($R_1$=$SO_3H$, $R_2$=H and $R_3$=H);

chondroitin sulfate D, which is predominantly sulfated in the carbon 2 position of glucuronic acid and in the carbon 6 position of the GalNAc sugar and is also known as 2,6-chondroitin sulfate ($R_1$=$SO_3H$, $R_2$=H and $R_3$=$SO_3H$);

chondroitin sulfate E, which is predominantly sulfated in the carbon 4 and 6 positions of the GalNAc sugar and is also known as 4,6-chondroitin sulfate ($R_1$=$SO_3H$, $R_2$=$SO_3H$ and $R_3$=H);

The term "chondroitin sulfate" also includes organic and inorganic salts thereof. Generally, such salts are prepared, for example, by means of reacting the basic form of this compound with a stoichiometric amount of suitable acid in water or in organic solvent or in a mixture of both. Generally, non-aqueous media such as ether, ethyl acetate, ethanol, isopropanol or acetonitrile, are preferred. Examples of inorganic salts include, for example, sodium, potassium, calcium, ammonium, magnesium, aluminum and lithium salts, and organic salts include, for example, ethylendiamine, ethanolamine, N,N-dialkylene-ethanolamine, triethanolamine, glucamine and basic amino acid salts. The salts are preferably pharmaceutically acceptable.

The functions of chondroitin largely depend on the properties of the entire proteoglycan of which it is a part. These functions can broadly be split into structural and regulating roles. However, this division is not absolute and some proteoglycans can carry out both structural and regulating roles.

With respect to its structural role, chondroitin sulfate is a primary component of the extracellular matrix and is important for maintaining the structural integrity of tissue. As part of an aggrecan, chondroitin sulfate is a primary component of cartilage. Highly charged sulfate groups and tightly packed groups of chondroitin sulfate generate electrostatic repulsions providing a lot of compressive strength to cartilage.

Keratan sulfate is a sulfated glycosaminoglycan similar to chondroitin sulfate in which the sulfate group is found in glucuronic acid. Specifically, it consists of galactose and GlcNAc-6-sulfate, bound by means of a β-1,4 bond.

It is mainly found in the cornea, cartilage and bone. At the joint level, it helps absorb mechanical impacts, reducing the effects of such impacts on surrounding structures. It participates in central nervous system development and in the mechanisms of protection activated when damage occurs in said central nervous system.

Carrageenan is formed by sulfated or non-sulfated galactose and/or anhydrogalactose units, bound by alternating α-1,3 and α-1,4 bonds. Several types of carrageenan are distinguished depending on the degree of sulfation, on the positions of the sulfate groups and on the presence of anhydrogalactose groups, with clearly different properties as hydrocolloids. The higher the proportion of sulfate groups, the higher the solubility, and the higher the proportion of anhydrogalactose groups, the lower the solubility. In the context of the present invention, all types of carrageenan are included. Some of them include, for example, kappa, iota and lambda (k, i and l) carrageenans.

Glucomannan is a water-soluble polysaccharide of natural origin. The chemical structure of this compound consists of a linear polymer chain with a small proportion of branching. Specifically, it is formed by D-mannose and D-glucose units bound by β-1,4 bonds at a ratio of 1.6:1, respectively.

In a particular embodiment of the invention, the glucomannan used is a negatively charged glucomannan derivative selected from phosphorylated derivatives, carboxymethyl and dicarboxy-glucomannans.

Gellan gum is a water-soluble polysaccharide of natural origin. The chemical structure of this compound consists of a polymer chain formed by α-L-rhamnose and β-D-glucuronic acid units and two β-D-glucose units.

It is depicted by means of the following structure:

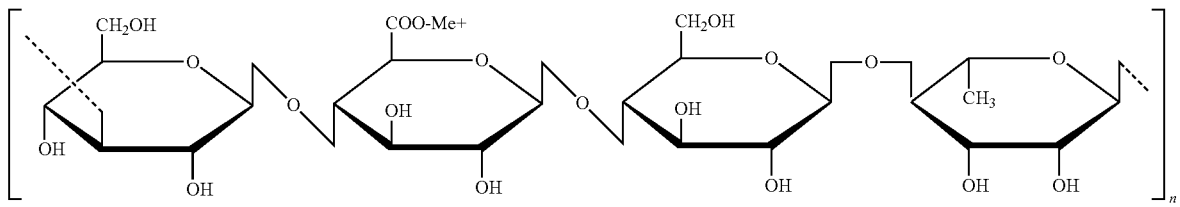

where n is an integer and represents the degree of polymerization, i.e., the number of monomer units in the gellan gum chain. The polymer can be found in partially acetylated form. Depending on its degree of acetylation, gellan gum provides gels with different mechanical properties.

In the context of the present invention, the term "gellan gum" includes all its different derivatives, as well as combinations thereof.

In a particular embodiment, the nanoparticles of the invention as previously described further comprise:
i) a cationic substance selected from the group consisting of ammonium salts, cationic polymers and fatty amines, and/or
ii) an anionic polymer selected from the group consisting of hyaluronic acid, colominic acid, polysialic acid, chondroitin, keratan, dextrans, heparin, carrageenans, furcellarans, alginates, agar-agar, glucomannan, gellan gum, locust bean gum, guar gum, tragacanth gum, acacia gum, xanthan gum, karaya gum, pectins, celluloses, starches, their salts, fragments, derivatives or combinations thereof The nanoparticles can optionally comprise an ethylene oxide derivative.

For the purposes of the present invention, "ethylene oxide derivative" is interpreted to mean a compound in which a —$CH_2CH_2O$— unit is repeated.

In a particular embodiment, the ethylene oxide derivative is a compound of formula I

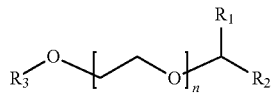

where $R_1$ is a hydrogen or carbonyl group; $R_2$ is an alkyl, alkenyl or alkynyl group having between 2 to 24 carbon atoms; $R_3$ is hydrogen or an alkyl group having between 1 to 6 carbon atoms; n is a value between 1 and 100. In a particular embodiment, n has a value of between 1 and 50, more preferably between 1 and 24.

Examples of ethylene oxide derivatives, without being limited to said examples, are polyethylene glycol dodecyl ether (Brij 30), polyethylene glycol hexadecyl ether (Brij 56), polyethylene glycol 2-octadecyl ether (Brij 72), polyethylene glycol 8-octadecyl ether (Brij 78), polyethylene glycol 8-stearate (Myrj 45), 2-hydroxyethyl octadecanoate (Myrj 52), ethylene glycol monostearate, triethylene glycol monostearate.

In a particular embodiment, the nanoparticles of the invention are characterized by being a homogenous solid matrix, the mean size of which is comprised between 1 and 999 nm, and consist of
  a) one or more sorbitan esters in a proportion by weight of between 60% and 100%, and
  b) a component selected from the group consisting of a cationic substance, an anionic substance, an ethylene oxide derivative, or combinations thereof, in a proportion by weight between 0% and 40% with respect to the total weight of the nanoparticle components.

In a more particular embodiment, the nanoparticles of the invention are characterized by being a homogenous solid matrix, the mean size of which is comprised between 1 and 999 nm, and consist of one or more sorbitan esters in a proportion by weight of between 60% and 99% and a component comprised between the group consisting of a cationic substance, an anionic substance, an ethylene oxide derivative, or combinations thereof, in a proportion by weight between 40% and 1% with respect to the total weight of the nanoparticle components.

Active Ingredient

The nanoparticles of the present invention provide systems with a high active ingredient association capacity. Therefore, according to another preferred embodiment, the nanoparticles of the present invention additionally comprise at least one active ingredient.

The term "active ingredient" refers to an ingredient or cell used in the treatment, cure, prevention or diagnosis of a disease, or used for improving the physical and mental wellbeing of humans and animals, as well as that ingredient or cell intended for destroying, blocking the action of, counteracting or neutralizing any harmful entity or organism, or any ingredient or cell used as a cosmetic or for hygiene, as well as that ingredient or cell intended for regenerating tissues in tissue engineering or in cell therapy.

The nanoparticles object of the present invention are suitable for associating active ingredients regardless of the solubility characteristics thereof. The association capacity will depend on the corresponding active ingredient, but in general terms it will be high for both hydrophilic ingredients and for those ingredients that are markedly hydrophobic.

In a particular embodiment, the active ingredient is selected from hormones, peptides, proteins, proenzymes or zymogens, enzymes, coenzymes, vitamins, lipid or lipophilic compounds, hydrophilic compounds, saccharide compounds, nucleic acid or nucleotide compounds, such as oligonucleotides, polynucleotides and cells, or combinations thereof.

Preferably, the active ingredient can:
  have anti-fungal, antiseptic or anti-inflammatory activity,
  be applied in tissue engineering, regenerative medicine or cell therapy, such as a growth factor, for example,
  be of interest in cosmetics or hygiene, such as a peptide or protein, for example, or else a nucleic acid derivative, such as a DNA plasmid, oligonucleotide, interfering RNA or a polynucleotide. The DNA plasmid incorporates genetic material to be introduced into cells and express proteins or it acts like an RNA precursor.

In this same sense according to a preferred embodiment, the active ingredient is siRNA. According to a preferred embodiment, the proportion of active ingredient incorporated in the nanoparticles is equal to or less than 25% by weight with respect to the total weight of the components thereof. However, the suitable proportion will depend in each case on the active ingredient to be incorporated, the indication for which it is used and the administration efficiency. According to another preferred embodiment, the proportion of active ingredient is between 0.5 and 2% by weight.

In another preferred embodiment, the nanoparticles of the present invention additionally comprise at least one marker. In the present invention, "marker" is interpreted to mean that element, compound, cell or group of cells that allows performing a location study thereof, obtaining an image, signal or information about the site or sites in which it is distributed, determining a biochemical, immunological or metabolic parameter, or performing a diagnosis. Examples of markers are a fluorescent molecule, such as fluorescein or Texas Network, for example; quantum dots; a radioactive isotope; a contrast agent, for example an X-ray, resonance or tomography contrast agent; a membrane antigen; a staining agent, etc.

According to another preferred embodiment, the nanoparticles of the present invention additionally comprise at least one compound capable of helping or reinforcing the effect of the active ingredient, such as an adjuvant, an immunomodulator (immunosuppressant or immunostimulator) or any combination thereof, for example.

According to another preferred embodiment, the nanoparticles of the present invention additionally comprise at least one compound interacting with biological components and/or components with affinity for one or several receptors existing in living beings and/or acting as a receptor of any biological component, such as an antibody, an aptamer, a surface receptor or any combination thereof. Some of the functions of these compounds interacting with biological components can be performing a location study of said biological components or receptors, producing an image, signal or information about the site or the sites where they are found, determining a biochemical, immunological or metabolic parameter, or performing a diagnosis.

According to another preferred embodiment, the nanoparticles of the present invention additionally comprise at least one stabilizing compound of a lipid, fatty or oily, or saccharidic type, an amino acid or protein derivative, an ethylene oxide derivative, a morpholine-type compound or any combination thereof.

According to another preferred embodiment, the nanoparticles of the present invention additionally comprise at least one compound sensitive to chemical polymerization or polymerization induced by UV/Vis radiation (photopolymerization), heat (thermal polymerization), microwaves, ultrasounds and X-rays.

According to another preferred embodiment, the nanoparticles of the present invention additionally comprise emollient agents, preservatives, perfume substances, anti-acne agents, antifungal agents, antioxidants, deodorants, antiperspirants, anti-dandruff agents, depigmenting agents, whitening agents, anti-seborrheic agents, dyes, tanning lotions, UV light absorbing agents, or any combination thereof.

According to another particular embodiment, the nanoparticles of the present invention are in lyophilized or dehydrated form.

As described above, the nanoparticles of the invention can be part of a nutritional composition. Said nutritional composition can be a food, a dietary supplement or a nutritional supplement. The nutritional compositions can include milk, yogurts, fruit and vegetable juices, desserts, baby products or dehydrated products. The addition of the nanoparticles to the nutritional composition is done by means of mixing and homogenizing according to the technical method for preparing each product. Additionally, other components such as vitamins can be added to the nutritional composition. Examples of these compounds are vitamins from groups A, B, C, D, E or mixtures thereof.

A particular embodiment relates to the use of the nanoparticles as defined above for the preparation of vaccines.

A preferred embodiment of the invention relates to the use of the nanoparticles as defined above for use in tissue engineering, regenerative medicine and cell therapy.

According to another preferred embodiment, the invention relates to the use of the nanoparticles as defined above as a marker.

According to another particular embodiment, the invention relates to the use of the nanoparticles as defined above for diagnostic purposes.

According to another preferred embodiment, the invention relates to the use of the nanoparticles as defined above for oral, buccal, sublingual, topical, ocular, nasal, pulmonary, otic, vaginal, intrauterine, rectal, enteric or parenteral administration.

According to a preferred embodiment, the invention relates to the use of the nanoparticles as defined above in the preparation of a cosmetic or personal hygiene product for administration on the skin, pilous and capillary system, nails, lips, external genital organs, teeth or mucous membranes.

According to a preferred embodiment, the invention relates to the use of the nanoparticles for gene therapy, gene silencing or genetic interference, or genetic vaccination.

According to a preferred embodiment, the invention relates to the use of the nanoparticles for causing the association, expansion or activation of cell populations or for manipulating or changing the biological characteristics of autologous, allogeneic or xenogeneic living cells, or living cells from cell cultures, and subsequently using said cells or cell groups to obtain a therapeutic, diagnostic or preventive effect, or for regenerative purposes, or to modify the production of compounds by said cells, or to adapt said cells and effectively associate them with microparticles or microcapsules, matrices and scaffolds.

According to a preferred embodiment, the invention relates to the use of the nanoparticles to facilitate, stimulate or modify the production of compounds by cells for the purpose of biotechnological production.

According to a preferred embodiment, the invention relates to the use of the nanoparticles for the purpose of hygiene or aesthetics, to neutralize or eliminate ectoparasites, to add scent, to modify the appearance of the surface of the body and/or to correct body odors and/or to protect the surface of the body or keep it in good condition.

According to a preferred embodiment, the invention relates to the use of the nanoparticles to modify, correct or introduce organoleptic properties or to improve stability in a medicinal product or in a cosmetic or personal hygiene product.

According to a preferred embodiment, the invention relates to the use of the nanoparticles to condition, modify or restore the characteristics of water, foods or nutritional supplements, as well as to modify, correct or introduce new organoleptic properties or to improve the stability thereof, and to facilitate or enable the administration of foods or nutrients to living beings.

Method of Preparation of the Nanoparticles

The method for the preparation of the previously described nanoparticles comprises the following steps:
 a) preparing an organic phase comprising a sorbitan ester in a proportion by weight of between 60% and 100%;
 b) mixing under stirring the solution obtained in a) with an aqueous solution.

The method of preparation of the nanoparticles of the invention is a simple method that does not require using injection or homogenization. The method takes place under mild conditions and despite the components having low hydrophilicity, the components do not need to be melted, preventing the degradation of bioactive molecules that are to be associated with the systems.

As described above, it is possible to incorporate different components into the nanoparticulate systems of the invention, which makes them extremely versatile in terms of physicochemical characteristics and interaction with other components. The incorporation of those additional components favors the systems of the invention associating both lipophilic molecules (e.g. oleylamine) and hydrophilic molecules (e.g. siRNA).

Said components that can additionally be comprised in the system, such as a cationic substance, an anionic substance, or both, for example, can be added to the organic phase of step a) or to the aqueous phase of step b), depending on the characteristics of the substance incorporated into the system. Therefore, in a particular embodiment, the organic phase of step a) and/or the aqueous solution of step b) further comprises a cationic substance, an anionic substance or both.

Alternatively, the additional components can be incorporated in a step c) after step b). Said step c) comprises the incubation of the dispersion of nanoparticles formed in step b) with a solution comprising a cationic substance, an anionic polymer or a combination of both. In another particular embodiment, the solution of the additional component of step c) is at a v/v ratio between 5/1 to 1/5 dispersion of nanoparticles/solution of the additional component, preferably at a 1/1 ratio.

Alternatively, it is possible to produce nanoparticles pegylated or modified with ethylene oxide derivatives. These nanoparticles pegylated or modified with ethylene oxide derivatives can be prepared in a single step and furthermore has the advantage of not requiring any chemical reaction to fix the ethylene oxide chains to the surface of the nanoparticles.

Therefore, in another particular embodiment the organic phase of step a) further comprises an ethylene oxide derivative.

The fatty acid lipophilic chain will therefore be anchored in the nanoparticulate structure, whereas the ethylene oxide chains will be found in the resulting nanoparticles, arranged on the surface thereof, as they are facing the aqueous phase during the formation process.

In a particular embodiment, the solvent of the organic phase is a water-miscible solvent. In a more particular embodiment, the solvent is selected from aliphatic alcohols, preferably ethanol. The use of ethanol favors its removal by means of evaporation and is further characterized by being more innocuous and having less effect on the molecules to be associated than any of the organic solvents normally used in preparing systems based on low hydrophilicity materials.

According to a preferred embodiment, the sorbitan ester is dissolved in the organic phase at a concentration of between 0.1 and 10 mg/ml, more preferably between 2 and 7 mg/ml.

According to a preferred embodiment, the charged components, anionic substances or cationic substances, are dissolved in the aqueous or organic phase, depending on their nature, at a concentration of between 0.01 and 1.0 mg/ml, more preferably between 0.2 and 0.5 mg/ml.

According to another preferred embodiment, at least one of the solutions of the constituents of the nanoparticulate system is heated before being mixed.

According to another preferred embodiment, the method further comprises the addition of an active ingredient and/or a compound selected from a marker, an adjuvant, an immunomodulator, an antibody, an aptamer, a surface receptor, a stabilizing compound, a compound sensitive to chemical polymerization or combinations thereof, in one of solutions a) or b), depending on the lipophilic or hydrophilic nature thereof. Alternatively, the method comprises the addition of an active ingredient and/or a compound selected from a marker, an adjuvant, an immunomodulator, an antibody, an aptamer, a surface receptor, a stabilizing compound, a compound sensitive to chemical polymerization or combinations thereof, in a step c) after step b).

According to another preferred embodiment, the method comprises an additional step after step b) or step c) in which the nanoparticles are subjected to a complete or partial dehydration process (lyophilization or desiccation, respectively). It is thus possible to conserve them during storage so that they maintain their initial characteristics and so that the volumes of product that are going to be manipulated are reduced. The lyophilization or desiccation process leads, respectively, to a completely or partially dehydrated product.

According to another preferred embodiment, the method comprises an additional step in which the partially dehydrated or lyophilized nanoparticles are regenerated. It is therefore possible to dehydrate the nanoparticles to produce a more stable product during storage and to subsequently regenerate or recover the nanoparticles by means of a process of resuspension in an aqueous medium. Regenerated nanoparticles maintain the properties characterizing fresh or recently prepared nanoparticles (prior to subjecting them to dehydration treatment).

The previously described nanoparticles are obtained by means of the method described above. The electrostatic interaction resulting between the different nanoparticle components in the process of preparation or after the incubation of the dispersion of nanoparticles once formed with optional components generates characteristic physical entities which are independent and observable.

A final aspect of the invention therefore relates to nanoparticles obtainable as described above.

To better understand the features and advantages of the present invention, reference will be made below to a series of examples which, in an explanatory manner, complete the preceding description without meaning in any way that said invention is limited to such examples.

EXAMPLES

For the description of some of the following examples reference is made to results obtained by means of the following techniques:

The morphological characterization of the nanoparticles was carried out by transmission electron microscopy. As a step prior to viewing the transmission electron microscopy (CM 12 Philips, Eindhoven, Holland), samples were stained using a 2% phosphotungstic acid solution. To that end, 10 μL of the nanoparticle suspension were added to a screen having a pore size of 400 μm coated with Formvar® film. After 1 minute, the sample was dried by capillarity with filter paper, gently touching the edge of the droplet with a piece of paper. The next step consists of staining per se with 10 μL of 2% phosphotungstic acid, which is left to act on the sample for 1 minute, after which time the excess liquid is dried again as discussed above. Then the screen is washed with water for 30 seconds to remove the excess phosphotungstic acid, then taking the same precautions to dry it. Finally, the samples are kept in the corresponding sample carrier inside a drier until observation.

The size of the nanoparticles was determined by means of the photon correlation spectroscopy (PCS) technique and by using a Zeta Sizer (Zeta Sizer, Nano series, Nano-ZS, Malvern Instruments, UK) to that end, obtaining the mean size of the population and the polydispersity index thereof. To that end, the samples were suitably diluted in Milli-Q water.

The zeta potential of the nanoparticles was determined by means of the laser scattering anemometry (LDA) technique and using a Zeta Sizer (Zeta Sizer, Nano series, Nano-ZS, Malvern Instruments, UK) to that end. To that end, the samples were suitably diluted in a millimolar KCl solution.

The efficiency of the association of genetic material with the nanoparticles was determined by means of the agarose gel electrophoresis technique. To that end, 1% agarose gel was prepared in TAE (Tris-Acetate-EDTA, 40 mM Tris, 1% acetic acid, 1 mM EDTA), pH 8 buffer with ethidium bromide (10 mg/ml, 5 ml) and a loading buffer and migration marker made up of glycerin (30%), bromophenol blue (0.25%) and xylene cyanol (0.25%) were used. A potential difference of 100 mV was applied for 30 minutes and free genetic material was used as a control.

As used in the following examples, the following polymers were acquired from different commercial establishments: hyaluronic acid (Bioibérica, Spain), chondroitin sulfate (Calbiochem, USA). The DNA plasmid pEGFP was acquired from Elim Biopharmaceuticals (CA, USA).

The interfering RNA (siRNA) siGAPDH was acquired from Ambion (USA). The different sorbitan esters, together with Brij® and Mirj® used in developing the nanoparticles, were acquired from Sigma (Spain).0.48-1.44

The remaining products indicated in the examples below were acquired from Sigma (Spain).

Example 1: Preparation of Nanoparticles Prepared Using Low Water-Solubility Components Incorporating a Sorbitan Ester Nanoparticles were prepared using as a component a 50:50 lactic and glycolic acid copolymer having a molecular weight of 14 KDa (Resomer® RG502S, Boehringer-Ingelheim, Ingelheim, Germany) (PLGA) according to the technique described by Gref et al., European Journal of Pharmaceutics and Biopharmaceutics, 51, 2001, 111-118. To that end, 25 mg of PLGA were dissolved in 2 ml of dichloromethane, and 25 ml of a 0.3% aqueous solution (w/v) of 50 k polyvinyl alcohol (30000-70000 g/mol, Aldrich, Spain) were added to this organic phase, both phases being emulsified with the help of a Branson ultrasonic tip at 40 W for 60 seconds. Then the organic solvent was rapidly removed by means of vacuum evaporation in a Buchi rotavapor (Germany). As shown in Table 1, the obtained nanoparticles have a mean size of 175 nm.

Nanoparticles were also prepared following the same protocol and using the aforementioned component together with sorbitan monooleate (Span® 80) at a PLGA:sorbitan ester ratio of 39:1. As can be seen in Table 1, when sorbitan ester is incorporated in a small percentage, the size of the obtained nanoparticles is similar to that obtained using only lactic and glycolic acid copolymer.

In addition, the attempt was made to prepare nanoparticles following the same protocol but using exclusively sorbitan ester. However, when sorbitan ester is used as a single component, an aggregate is obtained, as shown in Table 1.

FIG. 1 shows a photograph of the nanoparticles prepared using PLGA:sorbitan ester at a ratio of 39:1 (left) and of the aggregate obtained when sorbitan ester is used exclusively (right).

TABLE 1

Characterization of the nanoparticles prepared using sorbitan monooleate (Span ® 80) (NP80) and other components such as lactic and glycolic acid copolymer (PLGA) or polyethylene glycol dodecyl ether (Brij) by means of the emulsion-evaporation technique (O/W).

| Formulation | Size (nm) | PDI |
|---|---|---|
| O/W PLGA | 178.7 ± 0.8 | 0.07 |
| O/W NP80-PLGA 39-1 | 174.3 ± 0.5 | 0.12 |
| 100% O/W NP80 | Aggregate | — |

In addition, the attempt was made to develop nanoparticles using the nanoprecipitation technique as described by Paolicelli et al., Nanomedicine, 5, 2010, 843-853, which technique is commonly used in developing lipid nanoparticles, and using a known surface-active agent such as polyethylene glycol dodecyl ether or Brij® 30. Specifically, an organic solution of Span® 80 (6.6 mg/ml) and Brij®30 (0.33 mg/ml) was prepared in methylene chloride and this solution was added to 30 ml of ethanol under stirring. This organic phase was added to an aqueous phase of 60 ml of Milli-Q water subjected to magnetic stirring. Then ethanol was removed in a rotavapor and the volume was concentrated to a final volume of 10 ml. The final result is a micellar solution and not nanoparticles. Evidence of this is left by the results obtained using the equipment normally used for determining nanoparticle size, which equipment in the described conditions does not allow detecting nanoparticles in suspension and therefore cannot perform the corresponding calculation of the mean nanoparticle size.

Example 2. Preparation of Nanoparticles Prepared Using Sorbitan Monooleate (Span® 80) and Surface Charge Modulation by Means of Incorporating Oleylamine (OA), Cetyltrimethylammonium Bromide (CTAB) and Benzalkonium Chloride (BZC)

An organic solution of Span®80 (6.6 mg/ml) in 30 ml of ethanol was prepared for the preparation of Span® 80 nanoparticles. This organic phase was added to an aqueous phase of 60 ml of Milli-Q water subjected to magnetic stirring, causing spontaneous nanoparticle formation. Then ethanol was removed in a rotavapor and the volume of the nanoparticle suspension was concentrated to a final volume of 10 ml.

In addition, nanoparticles were prepared incorporating oleylamine (OA), cetyltrimethylammonium bromide (CTAB) or benzalkonium chloride (BZC), for the purpose of modulating the surface charge of the particles and improving their interactions with negatively charged molecules, such as genetic material, for example, allowing their association. To that end, said components were incorporated in the ethanol phase at a concentration of 0.33 mg/ml, and the method described above was followed.

The obtained systems were characterized using the previously described techniques. The characterization results of the systems are shown in Table 2.

TABLE 2

Characterization of the nanoparticles prepared using sorbitan monooleate (Span ® 80) (NP80). The incorporation of OA, CTAB or BZC into said nanoparticles (NP80OA, NP80CTAB or NP80BZC) was done for the purpose of modulating the surface charge of said nanoparticles.

| Formulation | Size (nm) | PDI | Zeta potential (mV) |
|---|---|---|---|
| NP80 | 156.2 ± 7.5 | 0.08 | −28.3 ± 4.6 |
| NP80OA | 136.1 ± 2.6 | 0.13 | +52.0 ± 3.1 |
| NP80CTAB | 172.1 ± 2.9 | 0.08 | +51.2 ± 1.5 |
| NP80BZC | 166.4 ± 4.8 | 0.08 | +43.6 ± 5.6 |

(PDI: polydispersity index)

As can be seen in Table 2, all the nanoparticulate systems have a homogenous particle size (characterized by a PDI value of about 0.1), with a mean diameter close to 150 nm. The nanoparticles prepared using exclusively Span® 80 have a negative zeta potential (of about −30 mV) and this potential can be modulated by means of incorporating cationic OA, CTAB or BZC molecules. Specifically, by using said molecules it is possible to completely reverse the surface charge from negative to positive, reaching values of around +50 mV.

The nanoparticulate systems were also observed by transmission electron microscopy to evaluate morphology. By way of example, FIG. 1 shows the morphology of the NPs prepared with Span® 80 and OA, Span® 80 and CTAB or Span® 80 and BZC.

Example 3. Preparation of Nanoparticles Prepared Using Sorbitan Monooleate (Span® 80) and Association of Interfering RNA (siRNA) as an Active Ingredient The nanoparticulate systems prepared using Span® 80 and with a positive surface charge due to the addition of OA, CTAB and BZC were used to associate an active ingredient. To that end, a negatively charged siRNA molecule was selected and incorporated into the mentioned nanoparticles by incubation. Specifically, the corresponding genetic material dissolved in Milli-Q water at a concentration of 0.10, 0.20 or 0.30 mg/ml in a volume of 200 microliters was incorporated into 200 microliters of the nanoparticle suspension (final siRNA concentration of 0.05, 0.10 or 0.15 mg/ml), the entire volume being kept in an incubator at 37° C. for two hours.

The characterization results of the systems are shown in Table 3.

TABLE 3

Characterization of the nanoparticles prepared using sorbitan monooleate (Span ® 80) associating interfering RNA (siRNA). The surface charge of said nanoparticles was modulated by means of incorporating OA, CTAB or BZC (NP80OA, NP80CTAB or NP80BZC).

| Formulation | siRNA (mg/ml) | Size (nm) | PDI | Zeta potential (mV) |
|---|---|---|---|---|
| NP80OA-RNA | 0.05 | 118.6 ± 3.2 | 0.10 | +49.6 ± 3.0 |
| NP80OA-RNA | 0.10 | 124.3 ± 5.8 | 0.10 | +38.3 ± 1.2 |
| NP80OA-RNA | 0.15 | 121.8 ± 3.3 | 0.09 | +36.2 ± 0.8 |
| NP80CTAB-RNA | 0.05 | 118.6 ± 3.2 | 0.08 | +42.8 ± 3.3 |
| NP80CTAB-RNA | 0.10 | 168.8 ± 2.5 | 0.10 | +41.6 ± 0.5 |
| NP80CTAB-RNA | 0.15 | 175.1 ± 3.6 | 0.08 | +42.9 ± 0.7 |
| NP80BZC-RNA | 0.05 | 171.4 ± 10.5 | 0.07 | +27.4 ± 0.6 |
| NP80BZC-RNA | 0.10 | 171.2 ± 10.6 | 0.09 | +27.3 ± 0.6 |
| NP80BZC-RNA | 0.15 | 170.6 ± 9.3 | 0.08 | +21.0 ± 1.3 |

(PDI: Polydispersity index).

Upon incorporating siRNA, a reduction of the positive zeta potential in relation to the blank system (without associated genetic material), the values of which are shown in Table 2 associated with Example 2, could be observed. This is because of the association of an anionic siRNA molecule with the surface of the nanoparticulate system.

Figure 3:
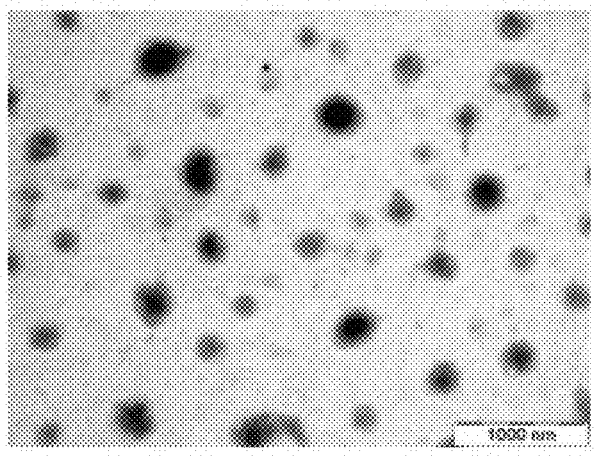
FIG. 3. Morphology of the nanoparticles associating siRNA prepared using Span® 80 and OA (A) or Span® 80 and BZC (B), observed by means of transmission electron microscopy at different magnifications.
Figure 3:
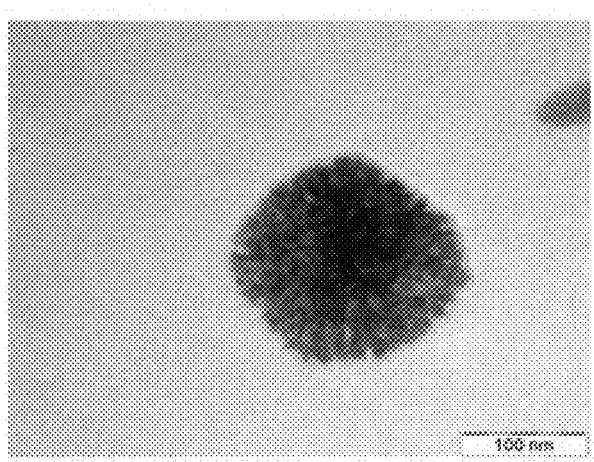

The nanoparticulate systems were also observed by transmission electron microscopy to evaluate morphology. By way of example, FIG. 3 shows the morphology of the nanoparticles associating siRNA prepared using Span® 80 and OA (top image) or Span® 80 and BZC (bottom image).

Figure 4:
FIG. 4. Results of the 1% agarose gel electrophoresis (100 V for 30 minutes). (A) 0.05 mg/ml free siRNA-GAPDH; (B) 0.15 mg/ml NP80OA associating siRNA-GAPDH; (C) 0.10 mg/ml NP80OA associating siRNA-GAPDH; (D) 0.05 mg/ml NP80OA associating siRNA-GAPDH; (E) 0.15 mg/ml NP80CTAB associating siRNA-GAPDH; (F) 0.10 mg/ml NP80CTAB associating siRNA-GAPDH; (G) 0.05 mg/ml NP80CTAB associating siRNA-GAPDH; (H) blank NP80OA (without siRNA) (I) blank NP 80CTAB (without siRNA) (NP80OA, NP80CTAB: nanoparticles prepared using Span® 80 and having the surface charge thereof modulated with OA or CTAB, respectively).

The association of siRNA with the systems could be confirmed by means of the agarose gel electrophoresis technique. FIG. 4 shows one of the gels obtained, specifically for systems prepared using Span® 80 and with their surface charge modified by means of incorporating OA or CTAB. Bands due to the presence of siRNA can be observed in said gel. As can be seen, when siRNA is deposited in free form, it migrates along the gel, giving rise to a characteristic band (A). The blank nanoparticles do not give rise to any band as siRNA (H and I) is not associated. In contrast, when siRNA was associated with the nanoparticles prepared using Span® 80 and OA, said band does not migrate and it remains in the output wells of the gel (B, C, and D), confirming that it is not in free form, but rather effectively associated with the nanoparticulate systems deposited in the wells of said gel. An intermediate situation is observed when siRNA is associated with the nanoparticles prepared using Span® 80 and CTAB. As can be seen, the association is effective at low siRNA concentrations, migration of the band (G) not being observed. However, at higher siRNA concentrations (E and F), there is a weak band leaving the wells, indicating partial migration of siRNA, or in other words, siRNA was not associated with the nanoparticles in its entirety.

The different association capacity observed by the nanoparticles may be because CTAB is a quaternary amine and therefore has a higher positive charge with which to associate siRNA with respect to OA (primary amine), the steric hindrance that may occur in CTAB could make it difficult to associate high concentrations of siRNA, unlike what occurs with OA.

Example 4. Preparation of Nanoparticles Prepared Using Sorbitan Monolaurate (Span®) 20) and Surface Charge Modulation by Means of Incorporating OA, CTAB and BZC Span® 20 nanoparticles were prepared according to the method previously described in Example 2. In addition to the nanoparticles prepared exclusively using sorbitan monolaurate (Span® 20), OA, CTAB and BZC were incorporated in other nanoparticle formulations for the purpose of modulating the surface charge of the nanoparticles and allowing the association therewith of negatively charged bioactive molecules, such as genetic material, for example.

Figure 10:
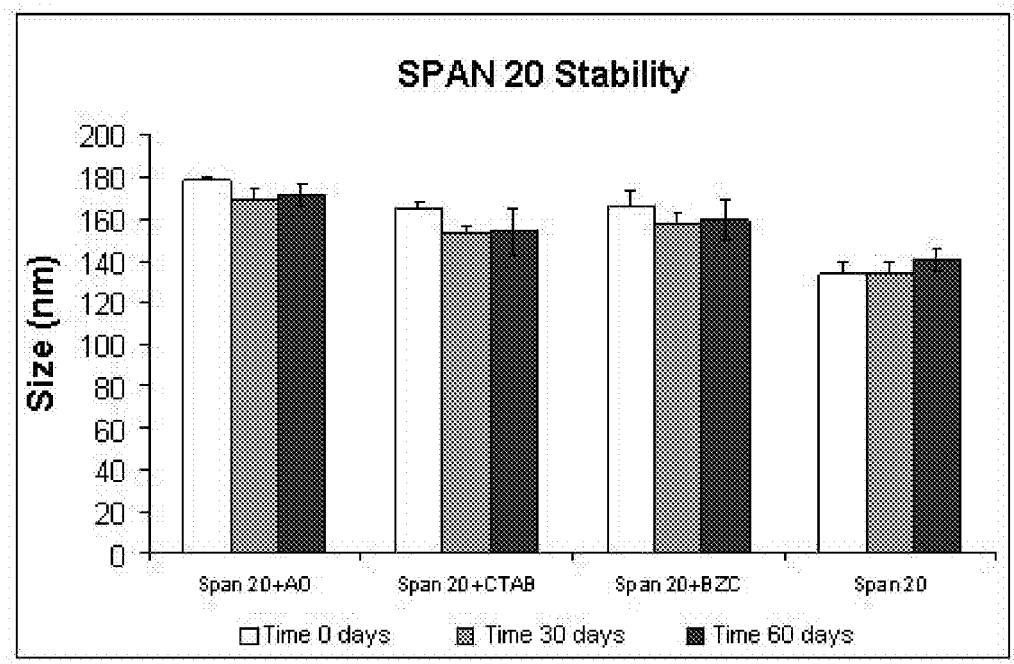
FIG. 10. Mean particle size of the formulations prepared with Span® 20 at time zero (recently prepared), thirty and sixty days after storage in a refrigerator at 4° C. (n=3).
Figure 11:
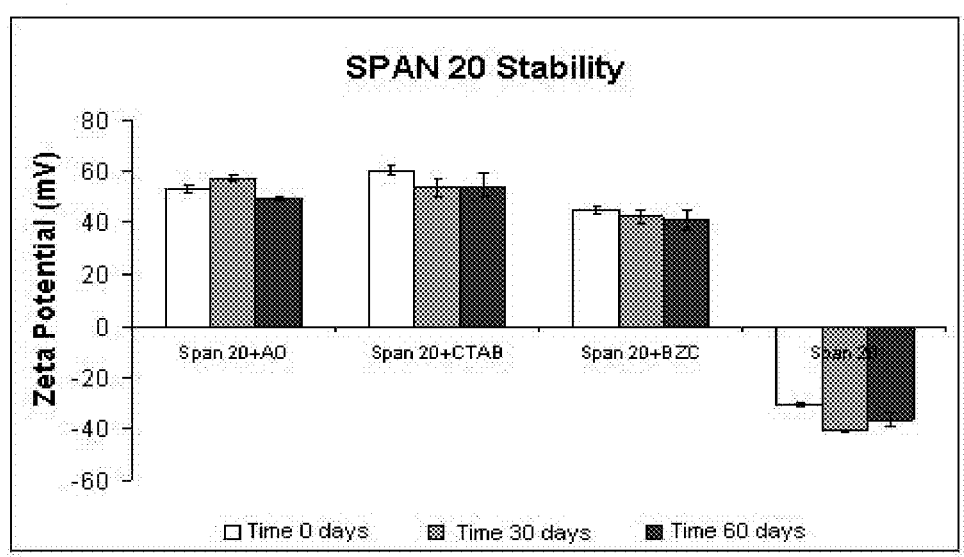
FIG. 11. Zeta potential of the formulations prepared with Span® 20 at time zero (recently prepared), thirty and sixty days after storage in a refrigerator at 4° C. (n=3).

The obtained systems were characterized using the previously described techniques. The characterization results of the systems prepared using Span® 20 and OA are shown in Table 4 and in FIGS. 10 and 11 in the columns corresponding to time 0. The characterization results of the systems prepared using Span® 20 and CTAB or BZC are shown in FIGS. 10 and 11 in the columns corresponding to time 0.

TABLE 4

Characterization of the nanoparticles prepared using Sorbitan monolaurate (Span ® 20) (NP20). The incorporation of OA (NP20OA) was done for the purpose of modulating the surface charge of said nanoparticles.

| Formulation | Size (nm) | PDI | Zeta potential (mV) |
|---|---|---|---|
| NP20 | 133.9 ± 5.6 | 0.09 | −30.7 ± 0.8 |
| NP20OA | 176.6 ± 7.4 | 0.09 | +54.1 ± 1.5 |

(PDI: Polydispersity index).

As can be seen in Table 4, the nanoparticulate systems have a homogenous particle size (characterized by a PDI value of about 0.1), with a mean diameter close to 140 nm. The nanoparticles prepared using exclusively Span® 20 have a negative zeta potential (of about −30 mV) and this potential can be modulated by means of incorporating the cationic OA molecule. Similar results were obtained using CTAB or BZC instead of OA, as shown in FIGS. 10 and 11 and Example 6. Specifically, by using said molecules it is possible to reverse the surface charge from negative to positive, reaching values of around +50 mV.

Figure 5:
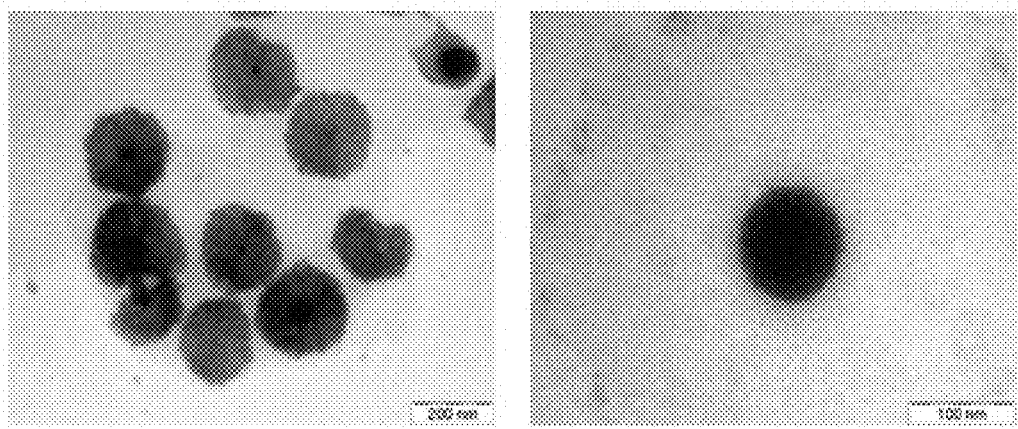
FIG. 5. Morphology of the nanoparticles prepared with Span® 20 and OA, observed by means of transmission electron microscopy at different magnifications.

The nanoparticulate systems were also observed by transmission electron microscopy to evaluate morphology. By way of example, FIG. 5 shows the morphology of the nanoparticles prepared with Span® 20 and OA.

Example 5. Preparation of Nanoparticles Prepared Using Sorbitan Monolaurate (Span® 20) and Association of Interfering RNA (siRNA) as an Active Ingredient The nanoparticulate systems prepared using Span® 20 and with a positive surface charge due to the addition of OA were used for associating an active ingredient. To that end, a negatively charged siRNA molecule was selected and incorporated into the mentioned nanoparticles by incubation, according to the methodology described in Example 3. The characterization results of the systems are shown in Table 5.

TABLE 5

Characterization of the nanoparticles prepared using sorbitan monolaurate (Span ® 20) associating interfering RNA (siRNA). The surface charge of said nanoparticles was modulated by means of incorporating OA.

| Formulation | siRNA (mg/ml) | Size (nm) | PDI | Zeta potential (mV) |
|---|---|---|---|---|
| NP20OA-RNA | 0.05 | 180.4 ± 15.7 | 0.10 | +40.6 ± 0.6 |
| NP20OA-RNA | 0.10 | 213.5 ± 18.3 | 0.13 | +32.2 ± 1.3 |

(PDI: Polydispersity index)

Upon incorporating siRNA, a reduction of the positive zeta potential in relation to the blank system (without associated genetic material), the values of which are shown in Table 5 associated with Example 5, could be observed. This is because of the association of an anionic siRNA molecule with the surface of the nanoparticulate system.

Figure 6:
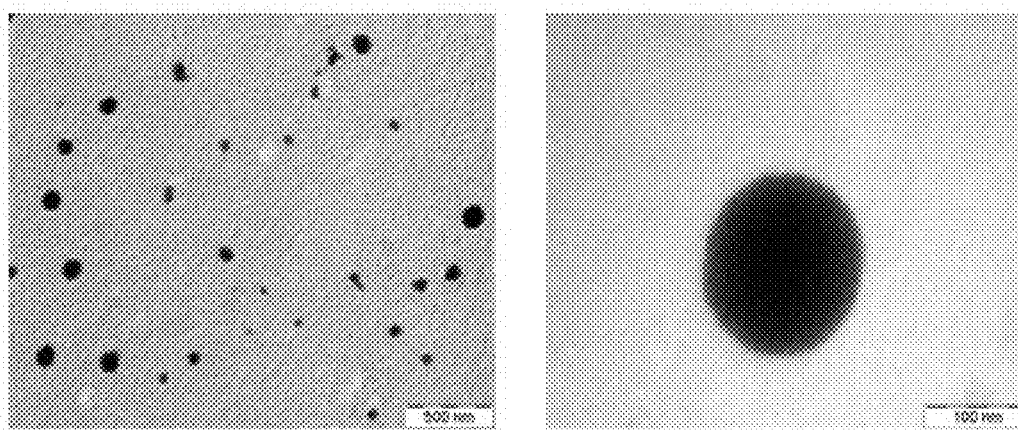
FIG. 6. Morphology of the nanoparticles prepared with Span® 20 and OA associating siRNA, observed by means of transmission electron microscopy at different magnifications.

The nanoparticulate systems were also observed by transmission electron microscopy to evaluate morphology. By way of example, FIG. 6 shows the morphology of the nanoparticles associating siRNA prepared using Span® 20 and OA.

Figure 7:
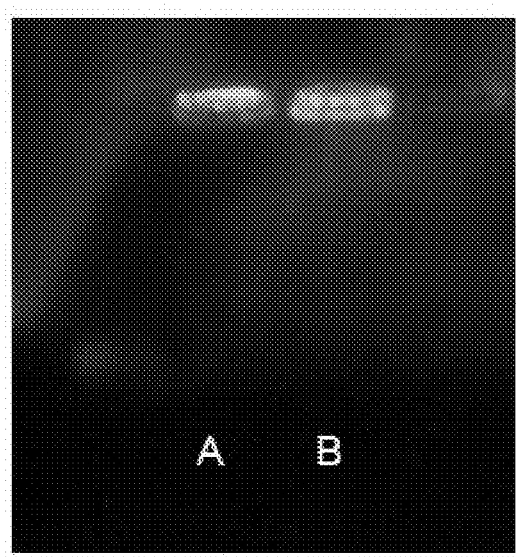
FIG. 7. Results of the 1% agarose gel electrophoresis (100 V for 30 minutes). (A) 0.10 mg/ml NP20OA associating siRNA-GAPDH; (B) 0.05 mg/ml NP20OA associating siRNA-GAPDH (NPOA: nanoparticles prepared using Span® 20 and having the surface charge thereof modulated with OA).
Figure 8:
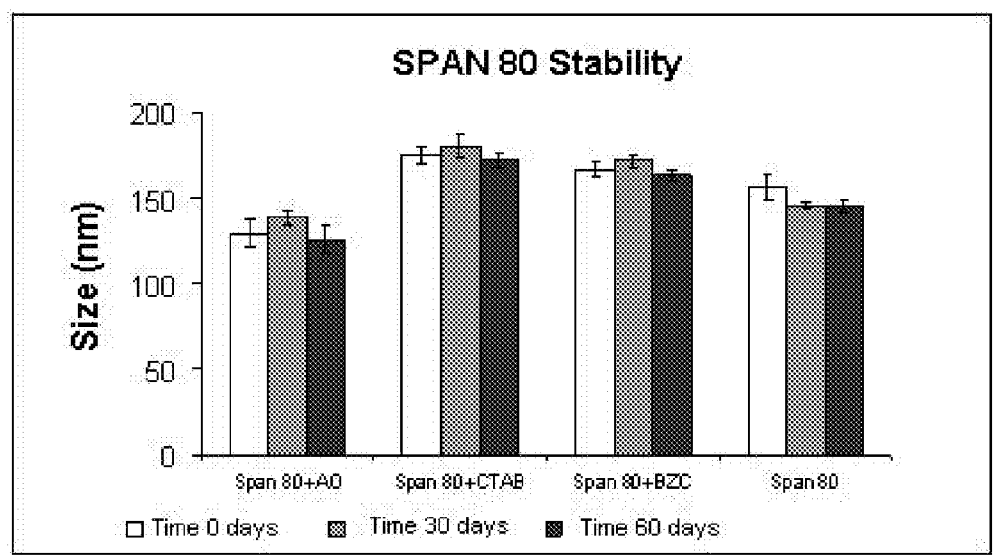
FIG. 8. Mean particle size of the formulations prepared with Span® 80 at time zero (recently prepared), thirty and sixty days after storage in a refrigerator at 4° C. (n=3).
Figure 9:
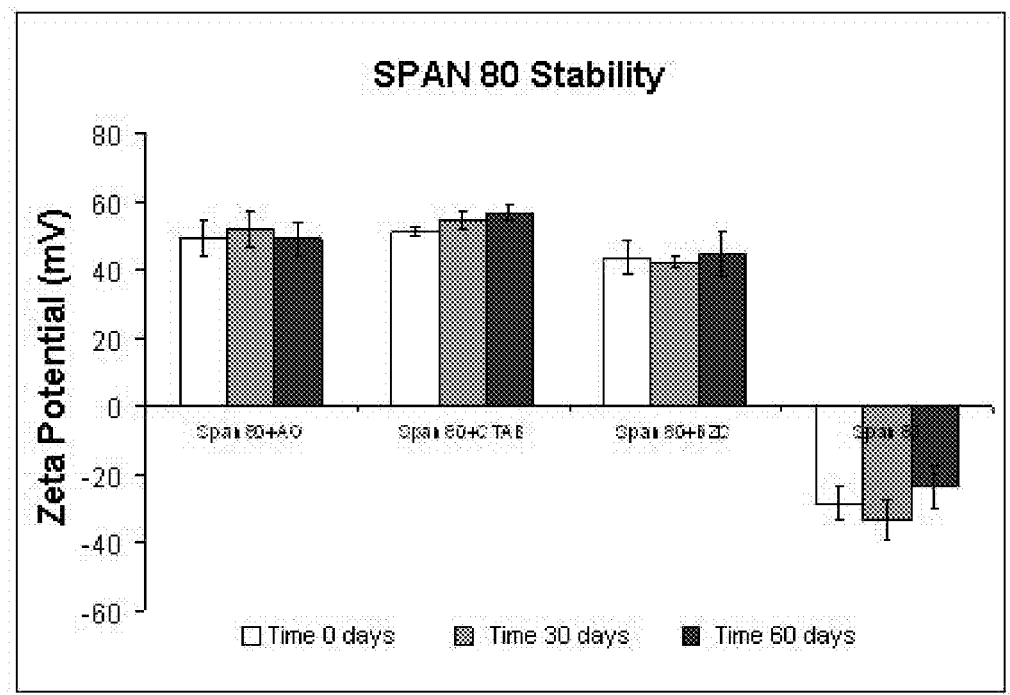
FIG. 9. Zeta potential of the formulations prepared with Span® 80 at time zero (recently prepared), thirty and sixty days after storage in a refrigerator at 4° C. (n=3).

The association of siRNA with the systems could be confirmed by means of the agarose gel electrophoresis technique. FIG. 7 shows one of the gels obtained, specifically for systems prepared using Span® 20 and with their surface charge modified by means of incorporating OA. Bands due to the presence of siRNA can be observed in said gel. As can be seen, when siRNA is deposited in free form, it migrates along the gel, giving rise to a characteristic band. In contrast, when siRNA was associated with the nanoparticles, said band does not migrate and it remains in the output wells of the gel, confirming that it is not in free form, but rather effectively associated with the nanoparticulate systems deposited in the wells of said gel.

Example 6. Study of the Stability of the Nanoparticles Prepared Using Span® 80 and Span® 20 with and without Charge Modulation by Means of Incorporating OA, CTAB and BZC The systems described in Examples 2 and 4 were subjected to a study of stability over time. To that end, the nanoparticle formulations were stored in refrigerator at 4° C. and after 30 and 60 days the mean particle size and zeta potential were compared with those determined for the recently prepared formulations (0 days). FIGS. 8, 9, 10 and 11 shows that the analyzed size and zeta potential parameters do not experience modifications throughout the period of time that is studied. The behavior shown by the developed formulations allows concluding that the nanoparticulate systems prepared using Span® 80 and 20 with or without surface charge modifications by means of incorporating OA, CTAB and BZC have good physical stability during the time the assay lasted, there being no significant differences in mean particle size and zeta potential over time for a significance level of 0.05% (Student's t-test).

Example 7. Preparation of Nanoparticles Prepared Using Sorbitan Trioleate (Span® 85) and Surface Charge Modulation by Means of Incorporating OA Span® 85 nanoparticles were prepared according to the method previously described in Example 2. Furthermore, nanoparticles incorporating OA were prepared for the purpose of modulating the surface charge of the particles and improving their interactions with negatively charged molecules, such as genetic material, for example.

To that end, organic solutions of Span® 85 (6.6 mg/ml) and OA (0.33 mg/ml) in 30 ml of ethanol were prepared. This organic phase was added to an aqueous phase of 60 ml of Milli-Q water subjected to magnetic stirring, causing spontaneous nanoparticle formation. Then ethanol was removed in a rotavapor and the volume of the nanoparticle suspension was concentrated to a final volume of 10 ml.

The obtained systems were characterized using the previously described techniques. The characterization results of the systems are shown in Table 6.

TABLE 6

Characterization of the nanoparticles prepared using sorbitan trioleate (Span ® 85) (NP85). The incorporation of OA into the nanoparticles (NP85OA) was done for the purpose of modulating the surface charge of said nanoparticles.

| Formulation | Size (nm) | PDI | Zeta potential (mV) |
|---|---|---|---|
| NP85 | 134.1 ± 12.6 | 0.09 | −32.9 ± 1.6 |
| NP 85OA | 201.2 ± 8.4 | 0.06 | +58.1 ± 1.9 |

(PDI: Polydispersity index)

As can be seen in Table 6, all the nanoparticulate systems have a homogenous particle size (characterized by a PDI value of about 0.1), with a mean diameter close to 170 nm. The nanoparticles prepared using exclusively Span® 85 have a negative zeta potential (of about −30 mV) and this potential can be modulated by means of incorporating the cationic OA molecule. Specifically, by using said molecule it is possible to reverse the surface charge from negative to positive, reaching values of around +60 mV.

Example 8. Preparation of Nanoparticles Prepared Using Sorbitan Monopalmitate (Span® 40) and Surface Charge Modulation by Means of Incorporating OA Span® 40 nanoparticles were prepared according to the method previously described in Example 2. Furthermore, nanoparticles incorporating OA were prepared for the purpose of modulating the surface charge of the particles and improving their interactions with negatively charged molecules, such as genetic material, for example.

To that end, organic solutions of Span® 40 (6.6, 3.3 or 1.65 mg/ml) and OA (0.33 mg/ml) in 30 ml of ethanol were prepared. This organic phase was added to an aqueous phase of 60 ml of Milli-Q water subjected to magnetic stirring, causing spontaneous nanoparticle formation. Then ethanol was removed in a rotavapor and the volume of the nanoparticle suspension was concentrated to a final volume of 10 ml.

The obtained systems were characterized using the previously described techniques. The characterization results of the systems are shown in Table 7.

TABLE 7

Characterization of the nanoparticles prepared using sorbitan monopalmitate (Span ® 40) at different concentrations. The incorporation of OA into the nanoparticles (NP40OA) was done for the purpose of modulating the surface charge of said nanoparticles.

| Formulation | Size (nm) | PDI | Zeta potential (mV) |
|---|---|---|---|
| NP40 (6.6 mg/ml) | 393.6 ± 71.3 | 0.48 | −23.5 ± 0.9 |
| NP40 (3.3 mg/ml) | 172.3 ± 1.5 | 0.27 | −24.3 ± 1.8 |
| NP40 (1.65 mg/ml) | 125.5 ± 1.49 | 0.16 | −22.2 ± 1.8 |
| NP40 (1.65 mg/ml) OA | 1523.0 ± 65.7 | 0.78 | +55.3 ± 1.7 |

(PDI: Polydispersity index)

As can be seen in Table 7, the nanoparticles prepared using Span® 40 at a concentration of 6.6 mg/ml have a mean size of about 400 nm but are characterized by low size distribution homogeneity (PDI of almost 0.5). In contrast, adjusting the Span® 40 concentration used allows developing nanoparticulate systems having a homogenous particle size (characterized by a PDI value of about 0.1), with a mean diameter close to 150 nm. The nanoparticles prepared using exclusively Span® 40 have a negative zeta potential (of about −20 mV) and this potential can be modulated by means of incorporating a cationic molecule, such as OA, for example. Specifically, by using said molecule it is possible to reverse the surface charge from negative to positive, reaching values of around +50 mV.

Example 9. Preparation of Nanoparticles Prepared Using Sorbitan Monooleate (Span® 80) and Incorporation of Chondroitin Sulfate or Hyaluronic Acid into the Surface Thereof in a Single Step Span® 80 nanoparticles were prepared according to the method previously described in Example 2 but incorporating into the aqueous phase molecules intended for coating the surface of the nanoparticles in a single step, such as chondroitin sulfate or hyaluronic acid. Taking into account that these molecules are negatively charged, the positively charged OA intended for modifying the surface charge of the nanoparticles and facilitating the association of chondroitin sulfate or hyaluronic acid by means of electrostatic-type interactions was incorporated into the organic phase.

To that end, organic solutions of Span® 80 (6.6 mg/ml) and OA (0.33 mg/ml) in 30 ml of ethanol were prepared. This organic phase was added to an aqueous phase of 60 ml of Milli-Q water into which chondroitin or hyaluronic acid was incorporated at a concentration of 0.33 mg/ml and it was subjected to magnetic stirring, causing spontaneous nanoparticle formation. Then ethanol was removed in a rotavapor and the volume of the nanoparticle suspension was concentrated to a final volume of 10 ml.

The obtained systems were characterized using the previously described techniques. The characterization results of the systems are shown in Table 8.

TABLE 8

Characterization of the nanoparticles prepared using sorbitan monooleate (Span® 80) incorporating chondroitin sulfate or hyaluronic acid (NPchondroitin, NPhyaluronic) into the surface thereof in a single step.

| Formulation | Size (nm) | PDI | Zeta potential (mV) |
|---|---|---|---|
| NPchondroitin | 142.9 ± 0.4 | 0.09 | −32.7 ± 0.7 |
| NPhyaluronic | 163.0 ± 0.1 | 0.12 | −24.3 ± 1.8 |

As can be seen in said table, all the nanoparticulate systems have a homogenous particle size (characterized by a PDI value of about 0.1), with a mean diameter close to 150 nm. The zeta potential values are characteristic of the polymers used in coating the surface of the nanoparticles. Specifically, the negative zeta potential of about −30 mV confirms the coating of the nanoparticles with these anionic polymers. These results clearly show the enormous versatility of the nanoparticles as regards composition and surface charge and the capacity using to that end a technique developed in a single step.

Example 10. Preparation of Nanoparticles Prepared Using Sorbitan Monooleate (Span® 80) and Incorporation of Polyarginine into the Surface Thereof in a Single Step Span® 80 nanoparticles were prepared according to the method previously described in Example 2 but incorporating into the aqueous phase a molecule intended for coating the surface of the nanoparticles in a single step, such as polyarginine. Taking into account that this molecule is positively charged, OA did not have to be incorporated into the organic phase like in Example 9, but rather only Span® was.

To that end, an organic solution of Span® 80 (6.6 mg/ml) in 30 ml of ethanol was prepared. This organic phase was added to an aqueous phase of 60 ml of Milli-Q water into which polyarginine was incorporated at a concentration of 0.33 mg/ml and subjected to magnetic stirring, causing spontaneous nanoparticle formation. Then ethanol was removed in a rotavapor and the volume of the nanoparticle suspension was concentrated to a final volume of 10 ml.

The obtained systems were characterized using the previously described techniques. The characterization results of the systems are shown in Table 9.

TABLE 9

Characterization of the nanoparticles prepared using sorbitan monooleate (Span® 80) incorporating polyarginine (NPpolyarginine) into the surface thereof in a single step.

| Formulation | Size (nm) | PDI | Zeta potential (mV) |
|---|---|---|---|
| NPpolyarginine | 229.7 ± 0.6 | 0.06 | +28.2 ± 0.8 |

As can be seen in said table, the nanoparticulate systems have a homogenous particle size (characterized by a PDI value of about 0.1), with a mean diameter close to 200 nm. The zeta potential values are characteristic of the polymer used in coating the surface of the nanoparticles. Specifically, the positive zeta potential of about +30 mV confirms the surface coating of the nanoparticles with the cationic polymer polyarginine, giving rise to a reversal of the negative charge of the nanoparticles prepared using Span® 80 without coating. These results clearly show the enormous versatility of the nanoparticles as regards composition and surface charge and the capacity using to that end a technique developed in a single step.

Example 11. Preparation of Nanoparticles Prepared from Sorbitan Esters Incorporating Macrogol Esters or Ethers The attempt was made in this example to incorporate macrogol esters and ethers into the nanoparticles because they have ethylene oxide or polyethylene glycol chains, which are of great interest for improving the interaction and stability of the nanoparticulate systems with and in biological media and barriers. These components having different polyethylene glycol chains and lipophilic chains were, specifically, those indicated in Table 9, where the composition thereof can be observed.

TABLE 10

Characteristics of the macrogol ethers and esters incorporated into the nanoparticles in a single step.

| Name | Formula | Brand |
|---|---|---|
| Polyethylene glycol dodecyl ether | $C_{12}H_{25}(OCH_2CH_2)_4OH$ | Brij ® 30 |
| Polyethylene glycol hexadecyl ether | $C_{16}H_{33}(OCH_2CH_2)_{10}OH$ | Brij ® 56 |
| Polyethylene glycol 2 octadecyl ether | $C_{18}H_{37}(OCH_2CH_2)_2OH$ | Brij ® 72 |
| Polyethylene glycol 8 octadecyl ether | $C_{18}H_{37}(OCH_2CH_2)_8OH$ | Brij ® 78 |
| Polyethylene glycol 8 stearate | $C_{18}H_{37}O(OCH_2CH_2)_8H$ | Myrj ® 45 |

The method described in Example 1 was followed for the preparation of the nanoparticles with these components. To that end, organic solutions of Span® 80 (6.6 mg/ml) and Brij® or Myrj® (0.33 mg/ml) in 30 ml of ethanol were prepared. This organic phase was added to an aqueous phase of 60 ml of Milli-Q water and subjected to magnetic stirring, causing spontaneous nanoparticle formation. Then ethanol was removed in a rotavapor and the volume of the nanoparticle suspension was concentrated to a final volume of 10 ml.

The obtained systems were characterized using the previously described techniques. The characterization results of the systems are shown in Table 11.

TABLE 11

Characterization of the nanoparticles prepared using sorbitan monooleate (Span ® 80) (NP80) and different Brij ® or Myrj ® molecules.

| Formulation | Size (nm) | PDI (mV) | Zeta potential |
|---|---|---|---|
| NP80-Brij ® 30 | 152.7 ± 0.8 | 0.07 | −28.9 ± 1.2 |
| NP80-Brij ® 56 | 138.9 ± 0.6 | 0.09 | −46.7 ± 1.4 |
| NP80-Brij ® 72 | 169.1 ± 2.5 | 0.17 | −47.8 ± 2.2 |
| NP80-Brij ® 78 | 147.7 ± 0.1 | 0.09 | −26.3 ± 1.1 |
| NP80-Myrj ® 45 | 151.7 ± 1.0 | 0.12 | −30.1 ± 1.6 |

As can be seen in said table, all the nanoparticulate systems have a homogenous particle size (characterized by a PDI value of about 0.1), with a mean diameter close to 150 nm. The zeta potential values varied depending on the characteristics of the ethylene oxide derivative used in preparing the nanoparticles, which is characteristic when using such molecules in coating surfaces. These results clearly show the enormous versatility of the nanoparticles as regards composition and surface charge and the capacity using to that end a technique developed in a single step.

In addition, it was found that it is only possible to obtain nanoparticles using a percentage of sorbitan esters comprised between one hundred percent and not less than sixty percent with respect to the total mass of the components used in preparing the nanoparticles.

Specifically, as shown in Table 12a, when the percentage of sorbitan ester is less than 60% with respect to the total mass of the components used in the preparation of the formulations, a clear micellar solution and not nanoparticles are obtained, taking into account that the equipment normally used for determining particle size does not detect nanoparticles in suspension and therefore cannot perform the corresponding calculation of the mean nanoparticle size.

TABLE 12a

Characterization of the nanoparticles prepared using sorbitan monooleate (Span ® 80) (NP80) and Brij ® 30.

| Formulation | Size (nm) | PDI |
|---|---|---|
| NP80-Brij ® 30 80%-20% | 163.9 ± 0.7 | 0.18 |
| NP80-Brij ® 30 60%-40% | 165.2 ± 1.5 | 0.37 |
| NP80-Brij ® 30 40%-60% | Absence | — |

(Absence: the Zeta Sizer does not detect nanoparticles)

Example 12. Lyophilization of the Nanoparticulate Systems Prepared from Sorbitan Esters and their Respective Modifications All the nanoparticulate systems described in the preceding examples were lyophilized using 5% trehalose or glucose as the cryoprotective agent at a nanoparticle suspension:cryoprotectant ratio of 1:1 and 1:2 (volume/volume). Tables 12b and 13 show the characterization results of recently prepared nanoparticles after lyophilization and subsequent resuspension.

TABLE 12b

Size of the recently prepared nanoparticulate systems after lyophilization and subsequent resuspension, using 5% glucose as the cryoprotective agent at a nanoparticle suspension:cryoprotectant ratio of 1:1 and 1:2 (volume/volume).

| Formulation | Initial size (nm) | Size (1:1) (nm) | Size (1:2) (nm) |
|---|---|---|---|
| NP80 | 151.0 ± 4.5 | 155.2 ± 4.3 | 146.5 ± 2.5 |
| NP80OA | 134.9 ± 1.8 | 147.3 ± 1.9 | 137.5 ± 2.7 |
| NP80CTAB | 171.1 ± 1.1 | 202.2 ± 8.6 | 176.7 ± 4.1 |
| NP80BZC | 171.4 ± 3.5 | 176.6 ± 3.9 | 169.9 ± 2.5 |
| NP20 | 133.9 ± 5.6 | 1721 ± 132 | 1125 ± 10 |
| NP20OA | 176.6 ± 7.4 | 3136 ± 1170 | 2905 ± 685 |
| NP20CTAB | 165.9 ± 3.7 | 359.8 ± 12.9 | 215.2 ± 6.8 |
| NP20BZC | 180.5 ± 6.2 | 239.3 ± 7.4 | 180.1 ± 2.7 |
| NP85 | 136.2 ± 1.0 | 688.7 ± 30.4 | 614.3 ± 49.8 |
| NP85OA | 192.3 ± 0.4 | 219.0 ± 4.1 | 208.1 ± 2.0 |
| NP40 | 125.5 ± 1.5 | 3181 ± 1933 | 8441 ± 483 |
| NP40OA | 1523 ± 65.7 | 1200 ± 212 | 1042 ± 44 |
| NPchondroitin | 142.9 ± 0.4 | 159.4 ± 2.3 | 143.2 ± 1.8 |
| NPhyaluronic | 163.0 ± 0.1 | 312.2 ± 11.9 | 168.0 ± 2.2 |
| NPpolyarginine | 229.7 ± 0.6 | 1851 ± 69 | 927.2 ± 16.8 |

TABLE 13

Size of the recently prepared nanoparticulate systems after lyophilization and subsequent resuspension, using 5% trehalose as the cryoprotective agent at a nanoparticle suspension:cryoprotectant ratio of 1:1 and 1:2 (volume/volume).

| Formulation | Initial size (nm) | Size (1:1) (nm) | Size (1:2) (nm) |
|---|---|---|---|
| NP80 | 151.0 ± 4.5 | 140.5 ± 3.7 | 135.1 ± 2.8 |
| NP80OA | 134.9 ± 1.8 | 143.7 ± 3.6 | 138.9 ± 5.9 |
| NP80CTAB | 171.1 ± 1.1 | 196.9 ± 3.6 | 220.7 ± 9.8 |
| NP80BZC | 171.4 ± 3.5 | 173.8 ± 3.0 | 178.0 ± 4.1 |
| NP20 | 133.9 ± 5.6 | 3255 ± 533 | 1513 ± 106 |
| NP20OA | 176.6 ± 7.4 | 6266 ± 3164 | 3438 ± 910 |
| NP20CTAB | 165.9 ± 3.7 | 402.0 ± 15.1 | 274.9 ± 5.6 |
| NP20BZC | 180.5 ± 6.2 | 240.8 ± 6.0 | 137.8 ± 5.4 |
| NP85 | 136.2 ± 1.0 | 235.1 ± 5.1 | 168.4 ± 5.2 |
| NP85OA | 192.3 ± 0.4 | 237.6 ± 3.6 | 236.6 ± 6.2 |
| NP40 | 125.5 ± 1.5 | 4760 ± 983 | 2742 ± 1192 |
| NP40OA | 1523 ± 65 | 4965 ± 2465 | 3749 ± 921 |
| NPchondroitin | 142.9 ± 0.4 | 164.6 ± 1.9 | 154.6 ± 4.2 |
| NPhyaluronic | 163.0 ± 0.1 | 243.0 ± 1.6 | 176.6 ± 7.2 |
| NPpolyarginine | 229.7 ± 0.6 | 1811 ± 83 | 526.5 ± 17.1 |

Figure 12:
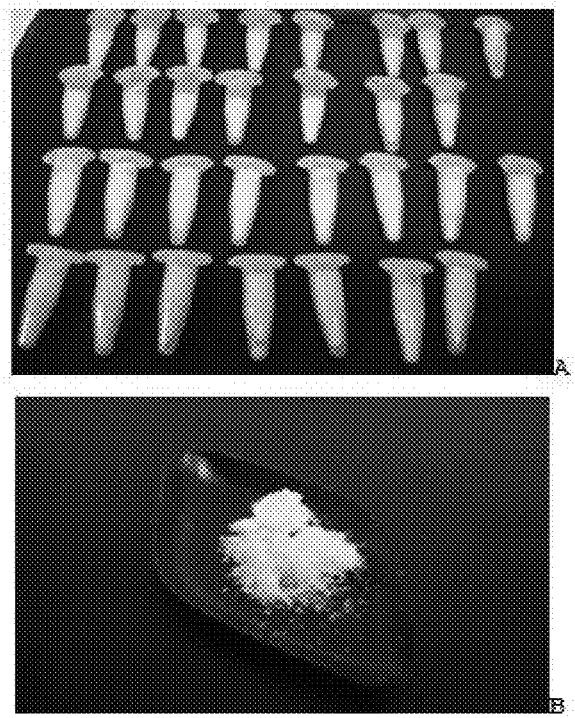
FIG. 12. Appearance of the nanoparticulate systems after lyophilization with 5% trehalose (A) and appearance of the lyophilized powder in detail (B).

The obtained results allowed verifying that by means of suitably selecting the cryoprotective agent type and concentration it is possible to obtain suitable powders from the suspensions of nanoparticles and that the mean particle size of said suspensions does not change in most formulations as a result of the lyophilization process, with the importance that it has in terms of optimizing the stability of the developed systems. By way of example, FIG. 12 shows the appearance of the nanoparticulate systems after lyophilization with 5% trehalose.

Example 13. Preparation of Nanoparticles Prepared Using Sorbitan Monooleate (Span® 80) and Association of an Antigenic Molecule as the Active Ingredient for the Development of a Nanovaccine In the present example, rPorB protein was associated with nanoparticles consisting of sorbitan esters for use as nano-vaccines. Specifically, the nanoparticulate systems prepared using Span® 80 and with a positive surface charge due to the addition of OA were used for associating said porin. Said porin was kindly donated by Professor Criado and Professor Ferreirós of the Microbiology Department of the Faculty of Pharmacy of University of Santiago de Compostela, at a concentration of 7 mg/ml in a 10 mM pH 7.4 Hepes medium, 0.1% SDS, 0.02% Thiomersal. For the association thereof with the nanoparticles, it was diluted in Milli-Q water to a concentration of 1 mg/ml, and this solution in a volume of 200 microliters was incorporated into 200 microliters of the nanoparticle suspension, the entire volume being kept in an incubator at room temperature for 90 minutes. The characterization results of the systems were the following: Size: 168.9±2.3 nm and Zeta potential: +54.5±2 mV. The protein association efficiency was calculated indirectly from the free protein recovered in the supernatant once the nanoparticles were centrifuged (14000 rpm, 120 min, 4° C.). The amount of free protein was determined using BCA quantitative technique, a 97% protein-nanoparticle binding being obtained for protein concentration of 1 mg/ml. Subsequently, Dot Blot, a qualitative technique that allows corroborating protein-nanoparticle binding, was performed and it again allowed confirming said nanoparticle-active ingredient association.

Example 14. Preparation of Nanoparticles Prepared Using Sorbitan Monooleate (Span® 80) and Association of Plasmid DNA as the Active Ingredient The nanoparticulate systems prepared using Span® 80 and with a positive surface charge due to the addition of OA were used for associating an active ingredient. To that end, a negatively charged model plasmid (pEGFP) molecule that was associated by means of incubation with the mentioned nanoparticles was selected. Specifically, the corresponding genetic material dissolved in Milli-Q water at a concentration of 0.3, 0.4, 0.5, 0.8 or 1 mg/ml in a volume of 100 microliters was incorporated into 100 microliters of nanoparticle suspension (final pDNA concentration of 0.15, 0.2, 0.25, 0.3, 0.4, 0.5 mg/ml), the entire volume being kept at room temperature under gentle mechanical stirring in a reciprocating shaker for 2 hours. The characterization results of the systems are shown in Table 14.

TABLE 14

Characterization of the nanoparticles prepared using sorbitan monooleate (Span ® 80) and with surface charge modulated by means of incorporating OA (NP80OA), associating plasmid DNA (pDNA).

| Formulation | pDNA (mg/ml) | Size (nm) | PDI | Zeta potential (mV) |
| --- | --- | --- | --- | --- |
| NP80OA | — | 200.5 ± 10.2 | 0.08 | +35.3 ± 3.5 |
| NP80OA-pDNA | 0.15 | 340.3 ± 15.3 | 0.13 | −11.1 ± 0.4 |
| NP80OA-pDNA | 0.2 | 287.1 ± 5.1 | 0.12 | −19.5 ± 1.5 |
| NP80OA-pDNA | 0.25 | 295.2 ± 8.3 | 0.14 | −20.5 ± 0.3 |
| NP80OA-pDNA | 0.3 | 317.6 ± 3.2 | 0.13 | −22.2 ± 0.4 |
| NP80OA-pDNA | 0.4 | 314.3 ± 5.2 | 0.14 | −20.4 ± 0.2 |
| NP80OA-pDNA | 0.5 | 337.7 ± 9.5 | 0.15 | −20.0 ± 1.8 |

(PDI: Polydispersity index)

By incorporating plasmid DNA, a change in the Zeta potential can be observed from positive in the blank particles (without associated genetic material) to negative values. This is due to the association of the anionic plasmid molecule with the surface of the nanoparticulate system, which confirms the process of association of the active ingredient with the nanosystems.

Figure 13:
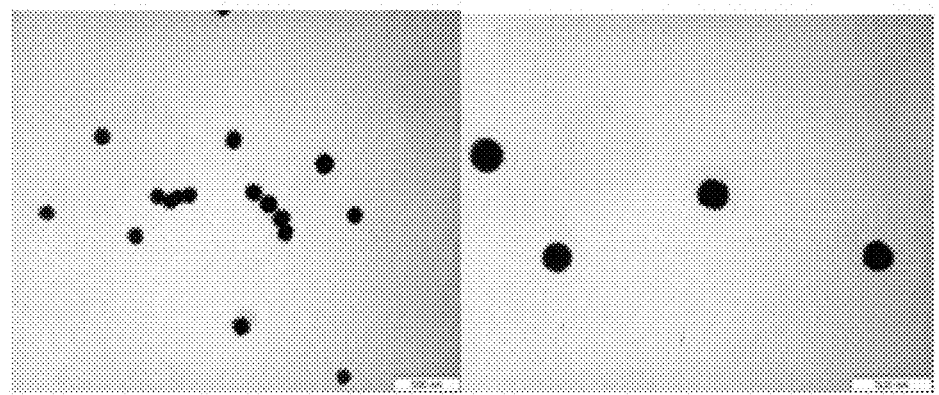
FIG. 13. Morphology of the nanoparticles associating model plasmid (pEGFP) prepared using Span® 80 and OA (NP80OA-pADN) observed by means of transmission electron microscopy at different magnifications.

The nanoparticulate systems were also observed by transmission electron microscopy to evaluate the morphology. By way of example, FIG. 13 shows the morphology of the nanoparticles associating pDNA prepared using Span® 80 and OA (NP80OA-pDNA).

Figure 14:
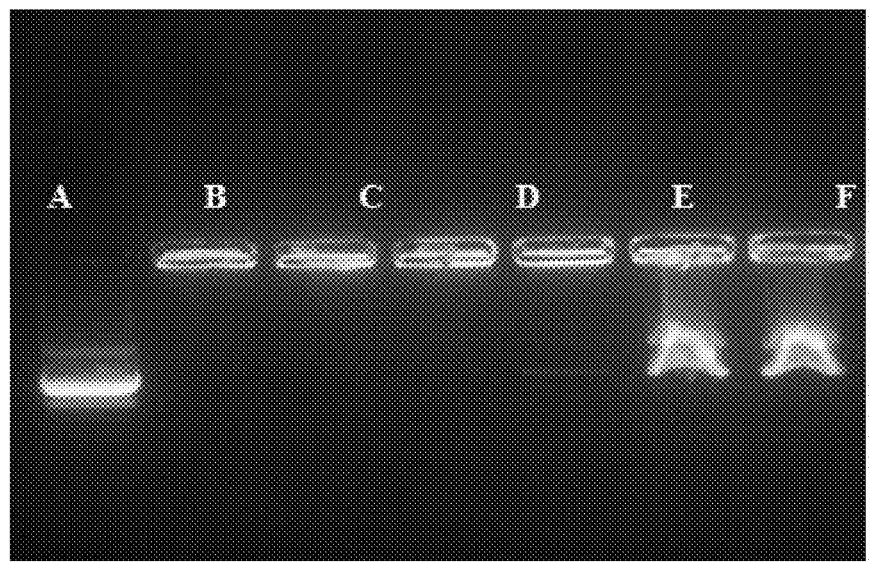
FIG. 14. Results of the 1% agarose gel electrophoresis (100 V for 30 minutes). (A) 0.15 mg/ml free pEGFP; (B) 0.15 mg/ml NP80OA-pEGFP; (C) 0.2 mg/ml NP80OA-pEGFP; (D) 0.25 mg/ml NP80OA-pEGFP; (E) 0.3 mg/ml NP80OA-pEGFP; (F) 0.4 mg/ml NP80OA-pEGFP; (G) 0.5 mg/ml NP80OA-pEGFP. (NP80OA-pEGFP: nanoparticles prepared using Span® 80 and having the surface charge thereof modulated with OA associating plasmid DNA pEGFP at a ratio of 1:1).

The association of the plasmid DNA with the systems can be confirmed by means of agarose gel electrophoresis technique. FIG. 14 shows one of the gels obtained specifically for the systems prepared using Span® 80 and with surface charge modified by means of incorporating OA. Bands can be seen in said gel due to the presence of plasmid. As can be seen, when the plasmid is deposited in free form, it migrates along the gel giving rise to a characteristic band (A). In contrast, when the plasmid was associated with the nanoparticles, said band does not migrate and it remains in the output wells of the gel (B, C, D, E), confirming that the plasmid is not in free form, but rather effectively associated with the nanoparticulate systems deposited in the wells of said gel, which prevents plasmid migration. Similarly, it can be observed that when the plasmid concentration DNA incubated with the nanoparticles is increased continuously, the system is not capable of associating any DNA, so it is observed that at least one part migrates along the gel (F and G).

Example 15. Transfection Efficiency of Nanoparticles Prepared Using Sorbitan Monooleate (Span® 80) and Associating Plasmid DNA as the Active Ingredient and the Expression of the Encoded Protein The systems described in the preceding example were selected to evaluate their cell transfection capacity and the corresponding expression of the encoded protein by the plasmid. Specifically, said systems are systems prepared using Span® 80 and with a positive surface charge due to the addition of OA (NP80OA), associating pEGFP at a final concentration of 0.2 mg of plasmid per ml of nanoparticle suspension (0.2 mg/ml NP80OA-pEGFP). The cell line used for the evaluation was the HEK-293 cell line, the expression of fluorescent green protein encoded by the plasmid being evaluated. To that end, the HEK-293 cells were seeded at a density of 200,000 cells per well in a 24-well culture plate (BD Flacon™) 24 h before the assay. At the time of the assay, the culture medium was replaced with 300 microL of HBSS containing free pEGFP or charged nanoparticles (0.2 mg/ml NP80OA-pEGFP) incubating them at different final plasmid concentrations (1, 2, 3 and 4 microg pEGFP/well). Lipofectamine 2000® (Invitrogen, Spain) was used as positive transfection control according to the manufacturer's instructions. The nanoparticles were incubated for 6 hours. After said time period, the cells were washed and 1 ml of fresh culture medium was added.

After 48 and 72 hours, positive cell transfection was evaluated by means of determining GFP detected by fluorescence microscopy (Eclipse TE 2000-S, Nikon UK Ltd., UK).

Figure 15:
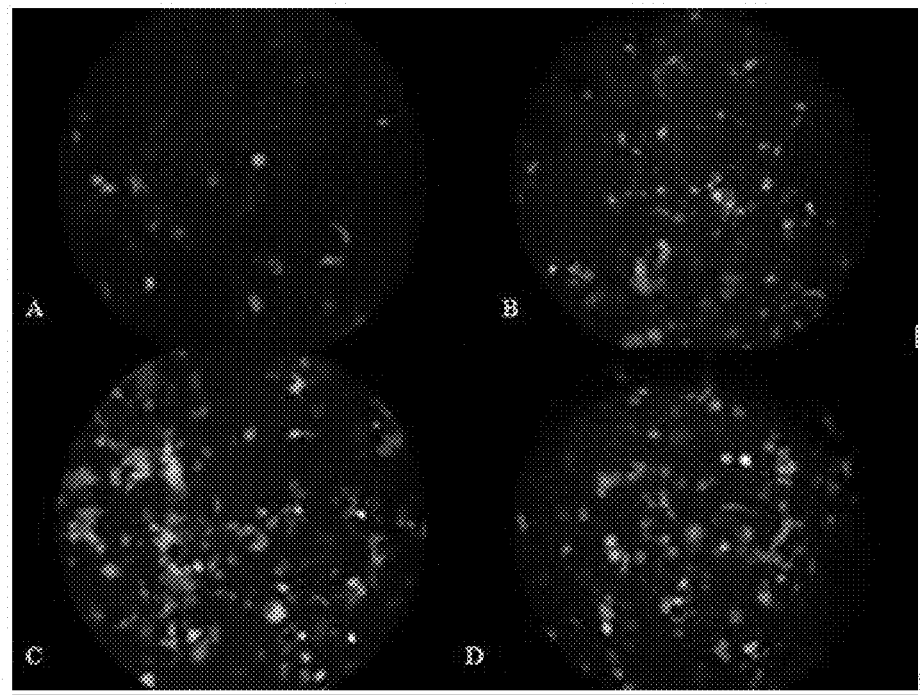
FIG. 15. Positive cellular expression of fluorescent green protein at 48 post-transfection with NP80OA-pEGFP nanoparticles at different final concentrations of plasmid per well. (A) 1 microg pEGFP, (B) 2 microg pEGFP, (C) 3 microg pEGFP, (D) 4 microg pEGFP.
Figure 16:
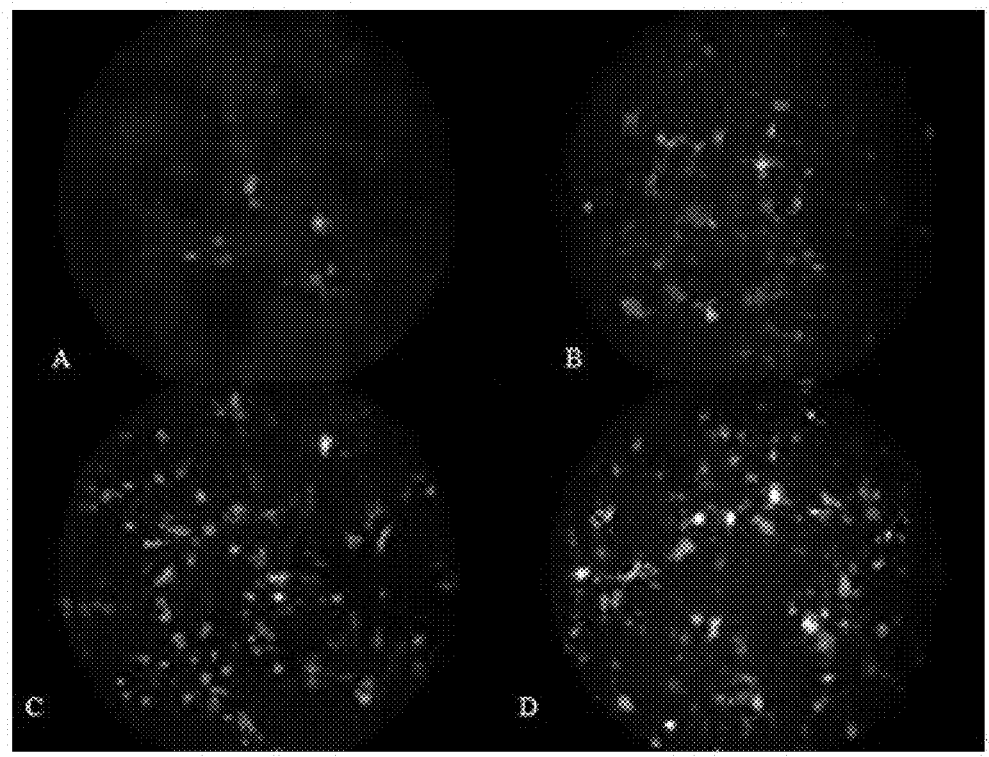
FIG. 16. Positive cellular expression of fluorescent green protein at 72 post-transfection with NP80OA-pEGFP nanoparticles at different final concentrations of plasmid per well. (A) 1 microg pEGFP, (B) 2 microg pEGFP, (C) 3 microg pEGFP, (D) 4 microg pEGFP.

As can be seen in FIGS. 15 and 16, the systems are capable of effectively transfecting the cells, which is confirmed by means of observing the corresponding expression of fluorescent green protein. As the amount of plasmid increases the presence of said protein increases, the transfection levels obtained with 3 microg being comparable to the transfection levels corresponding to 4 microg of plasmid associated with the nanoparticles.

Example 16. Confirmation of the Solid Matrix Structure of the Nanoparticles of the Invention The solid matrix structure of the nanosystems of the invention is demonstrated in the present example, which solid matrix structure differs from other structures that may comprise sorbitan as surfactant and that are not solid matrix structures but rather flexible structures in the form of single- or multilayer micelles, liposomes or niosomes, all such structures are known in the state of the art for their poor stability. To that end, sophisticated magnetic resonance techniques that allow characterizing the composition and supramolecular structure thereof were used.

The NMR spectra were acquired in an 17.6 T Inova Agilent (Varian) spectrometer (proton resonance frequency of 750 MHz) equipped with a triple resonance probe 1H/13C/31P and triple-axis shielded gradients XYZ. The samples were prepared by dissolving a few milligrams of the product to be studied (10 mg of Span 80 and 10 mg of OA) in 600 microliters of $H_2O$. The sample thus dissolved is introduced into conventional NMR tube 5 mm in diameter. For deuterium lock, a narrow glass capillary tube filled with deuterated DMSO was used. This capillary tube is inserted coaxially along the entire length of the sample tube and particularly inside the active sample volume detected by the probe. The content thereof does not contact the solution to be studied and therefore does not alter their properties.

Nanoparticles consisting of sorbitan monooleate, Span® (SP80, a sorbitan ester resulting from esterifying a hydroxyl group with the oleic acid) into which there was optionally incorporated a cationic substance, the fatty amine oleylamine (OA), which allows modulating the characteristics of the nanoparticulate systems, were selected as model formulations to be studied.

The nanoparticles developed from said components are abbreviated as NP80 and NP80OA, respectively, like in the preceding examples.

The results obtained from the different resonance studies conducted and the conclusions drawn are shown below.

One-Dimensional Proton Spectrum (1D 1H):

By comparing the $^1$H-NMR spectra of the nanoparticles NP80 and NP80OA (FIG. 17, top image and bottom image, respectively) with the spectra of the isolated Span 80 and OA molecules individually (FIG. 18, top image and bottom image, respectively) it is observed that the signals corresponding to the nanoparticles of the system are much broader. This observation is in accordance with the fact that the Span® 80 and the OA in the nanoparticles form part of a macromolecular species. Much narrower signals of the type shown in FIG. 18 would be seen if it is merely a free molecule (SP80 or OA) in the solution, because the proton spectra of the pure compounds have a smaller signal width and a higher signal resolution. In contrast, a larger NMR signal width means a lower molecular mobility.

It must be clarified that in the area between 3-3.7 ppm there is a series of narrow signals with a little intensity. It relates to a small proportion of low molecular weight impurities as confirmed with the 1H-Dfilter spectrum (see below).

1H-DFilter (Diffusion Filter) Spectrum:

The echo sequence stimulated with 4=350 ms, 5=1 ms and gradient of 65 G cm$^{-1}$ was used for this experiment. This NMR experiment provides a proton spectrum in which the signal intensity of small-size molecular species (low molecular weight compounds) is attenuated to a greater extent and the signal intensity of large-size molecular species (molecule or molecular aggregate with high molecular mass) is attenuated to a lesser extent. The effect of attenuation can be more clearly seen if this spectrum is compared to the 1D 1H spectrum in which the signals are not attenuated and therefore appear with their natural intensity.

Figure 17:
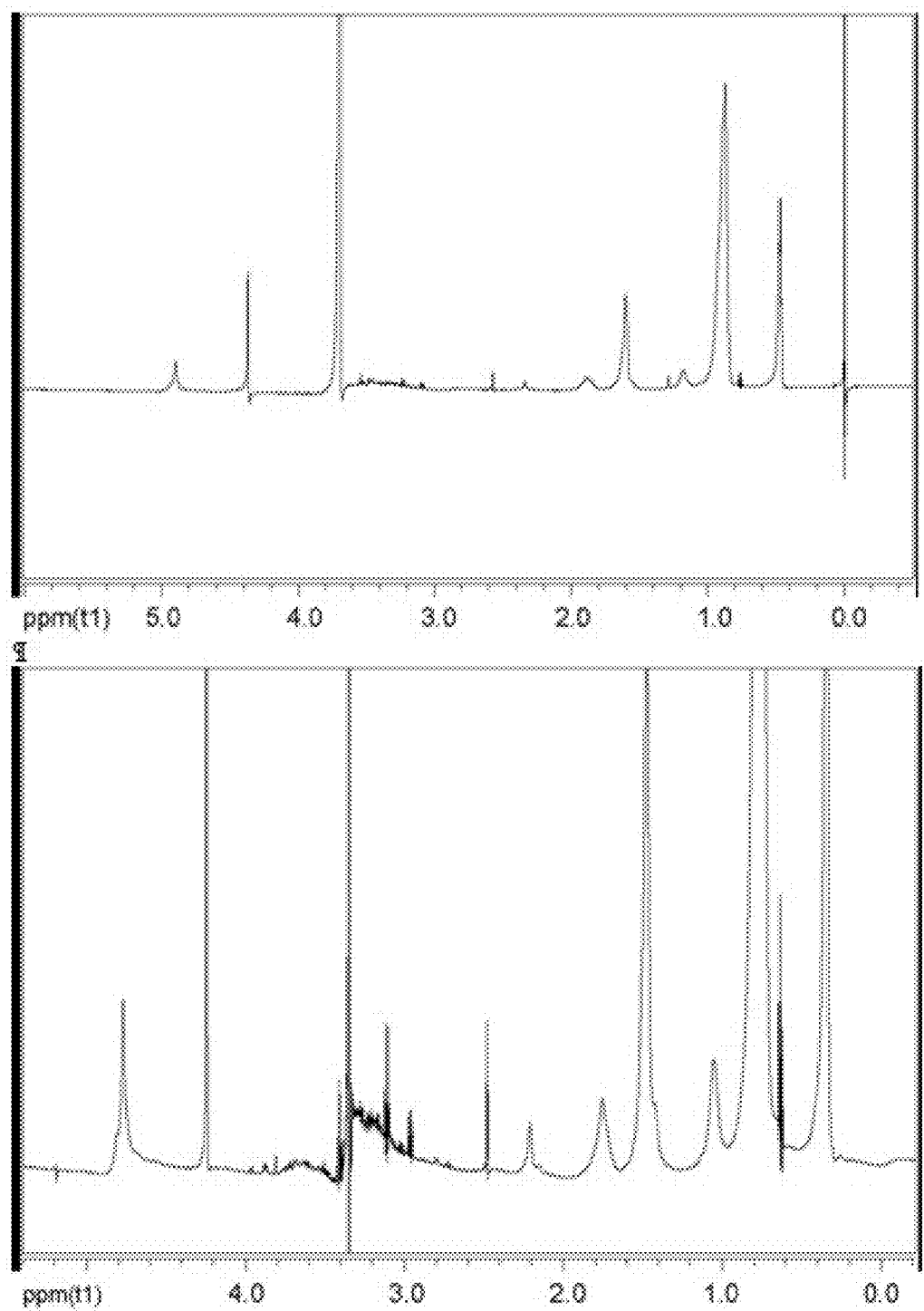
FIG. 17. One-dimensional proton spectrum ($^1$H-NMR) of the nanoparticles of Span® 80 (NP80) (top image) and the nanoparticles of Span® 80 incorporating oleylamine (NP80OA) (bottom image).
Figure 18:
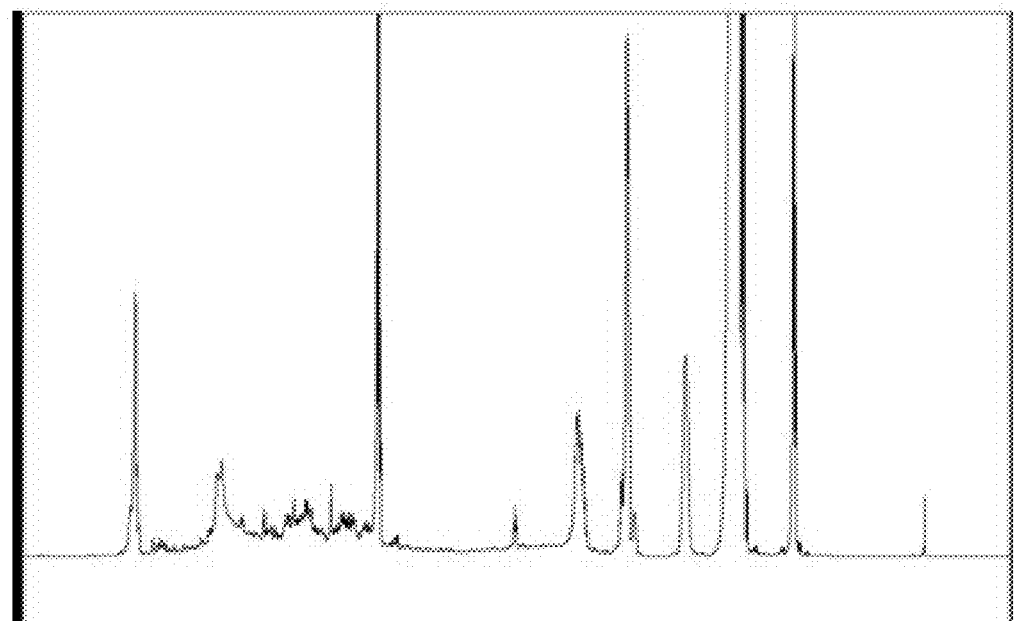
FIG. 18. One-dimensional proton spectrum ($^1$H-NMR) of the Span® 80 molecule (top image) and the oleylamine (OA) molecule (bottom image).
Figure 18:
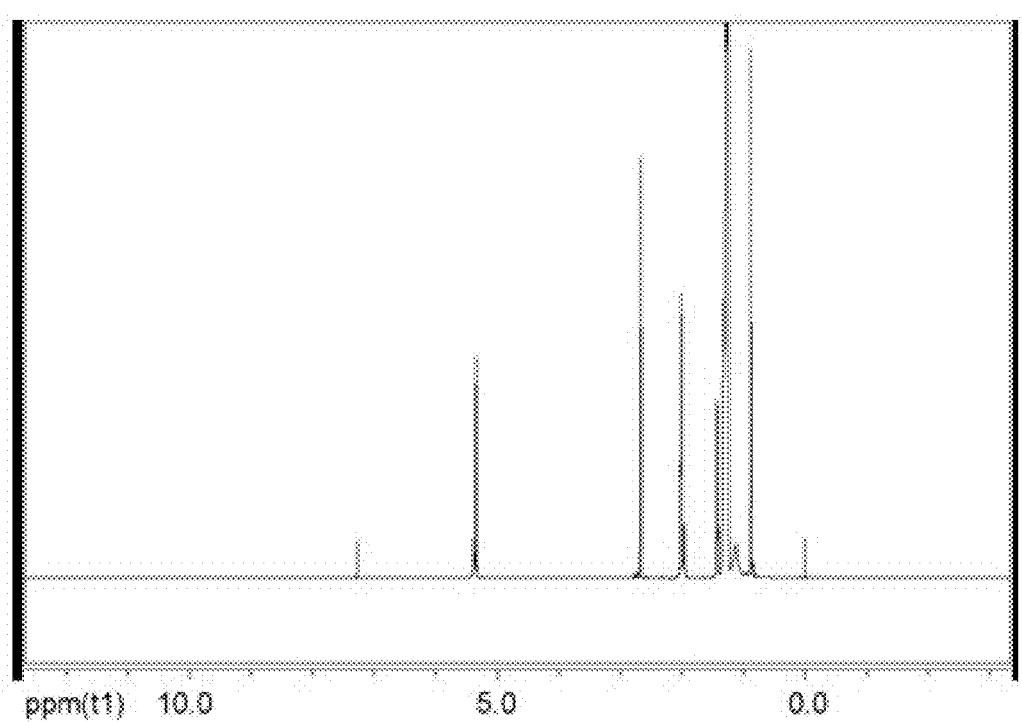
Figure 19:
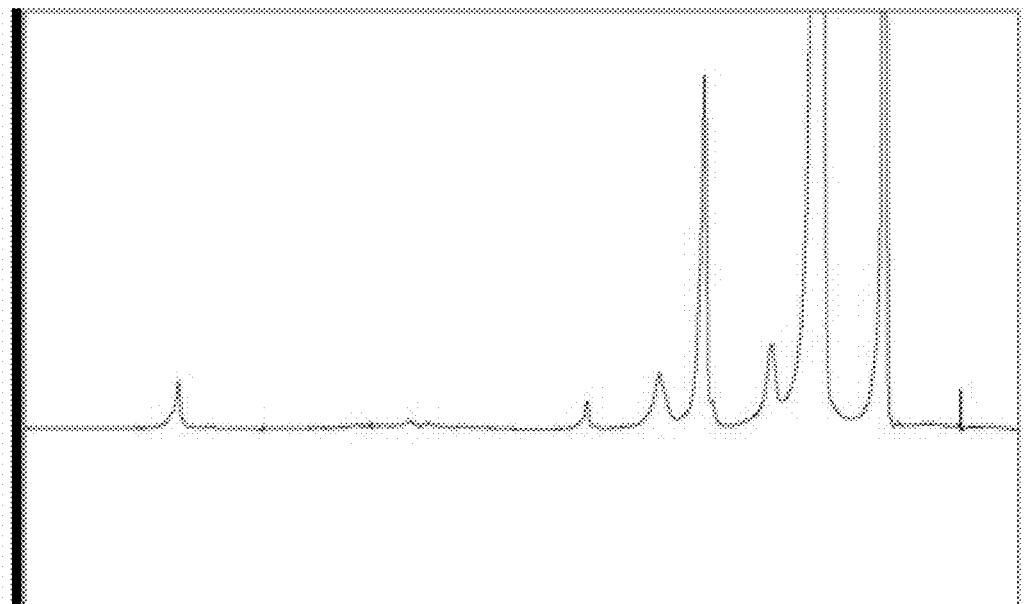
FIG. 19. 1H Dfilter spectrum for formulations NP80 (top image) and NP80OA (bottom image). An echo sequence stimulated with $\Delta$=350 ms, $\delta$=1 ms and a gradient of 65 G cm-1 was used.
Figure 19:
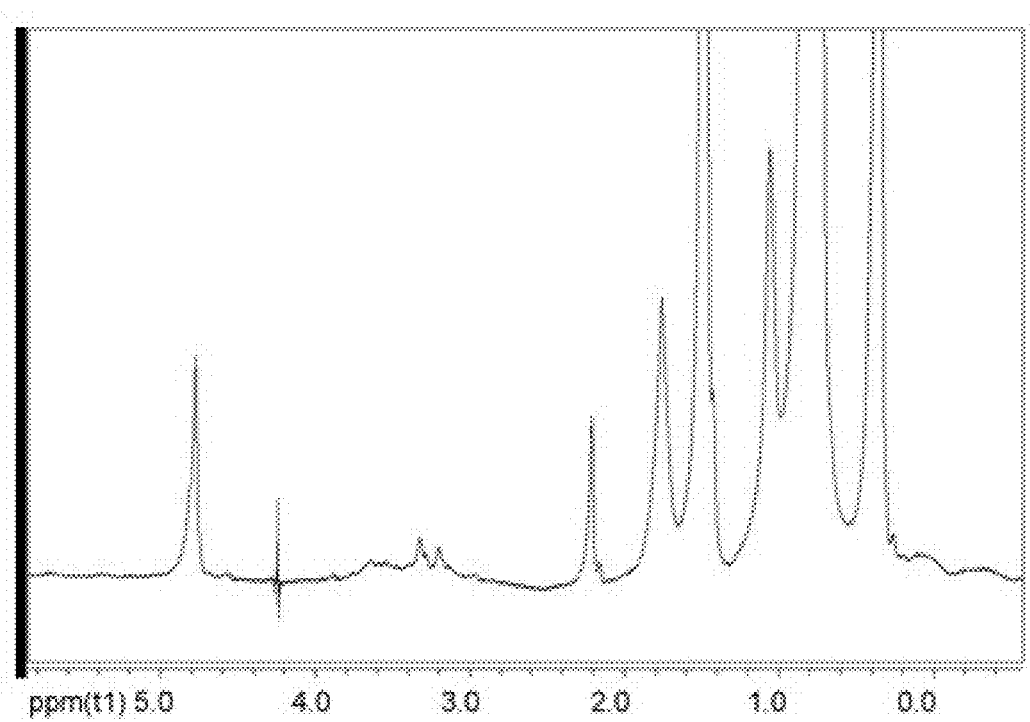

Therefore, if the 1H-Dfilter spectra obtained for the nanoparticles of the invention NP80 and NP80OA (FIG. 19) are compared to the spectra of FIG. 17, it is observed that the broad signals of FIG. 17 remain in the diffusion filter spectra as broad signals. In contrast, the signals corresponding to the solvents of the experiment and those corresponding to other low molecular weight impurities in the area between 3-3.7 ppm disappear. Furthermore, FIG. 19 better shows the broad signals between 3.9 and 4.2 ppm which were previously masked with the low molecular weight impurities, and are now revealed as broad signals corresponding to the cyclic structure of the sorbitan.

In conclusion, it is observed in these spectra that the signals of low molecular weight impurities disappear completely and the signals of SP80 and of OA does not alter much.

Based on the joint analysis of the proton and diffusion spectra, it can be concluded that the SP80 and SP80-OA molecules in the nanosystems of the present invention are neither isolated nor not in solution but rather form part of a supramolecular species with large dimensions.

STD Spectrum:

Spectra reflecting intra- and intermolecular proton interactions can be obtained with this saturation transfer-based experiment. Three STD spectra were obtained by selectively saturating in each of them a different position of the spectrum. Positions of 0.12, 0.78 and 5.5 ppm were saturated.

A control STD experiment was conducted with saturation at 0.78 ppm specifically affecting SP80 methyl signal. The spectrum obtained shows all the signals of the SP80 molecule (but not the impurities). This transfer from the methyl signal to all the signals of Span® 80 is consistent with the fact that the molecule forms part of a large molecular size aggregate (with a size much larger than that expected for the free molecule), which is also consistent with the large width of the aforementioned signals.

Figure 20:
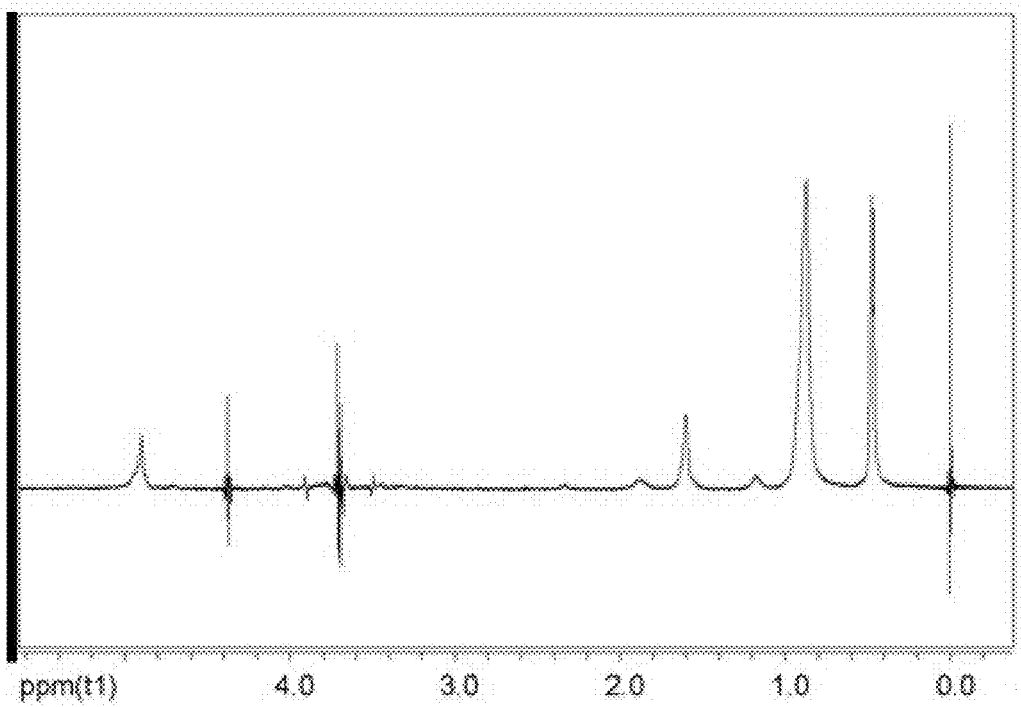
FIG. 20. 1D STD spectrum (STDoff-STDon difference) with selective saturation at 0.12 ppm for formulations NP80 (top image) and NP80OA (bottom image).
Figure 20:
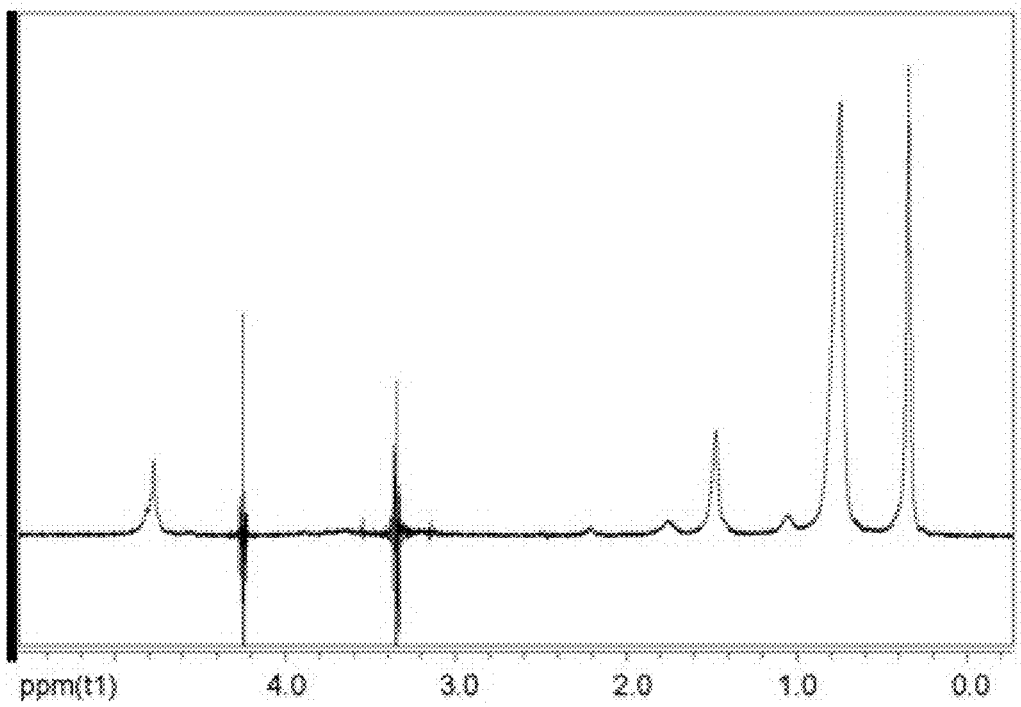

The STD experiment with saturation at 0.12 ppm is shown in FIG. 20. This saturation position corresponds with a area of the spectrum where proton signals are not seen. In principle, the saturation of a position without signals of the spectrum should give rise to a 1D STD spectrum completely void of signals because no saturation transfer whatsoever can be carried out. However, the opposite is observed and all the signals with large width that were previously observed in the spectra of the nanoparticles of the invention NP80 and NP80OA (FIG. 17) appear in the spectrum.

Figure 21:
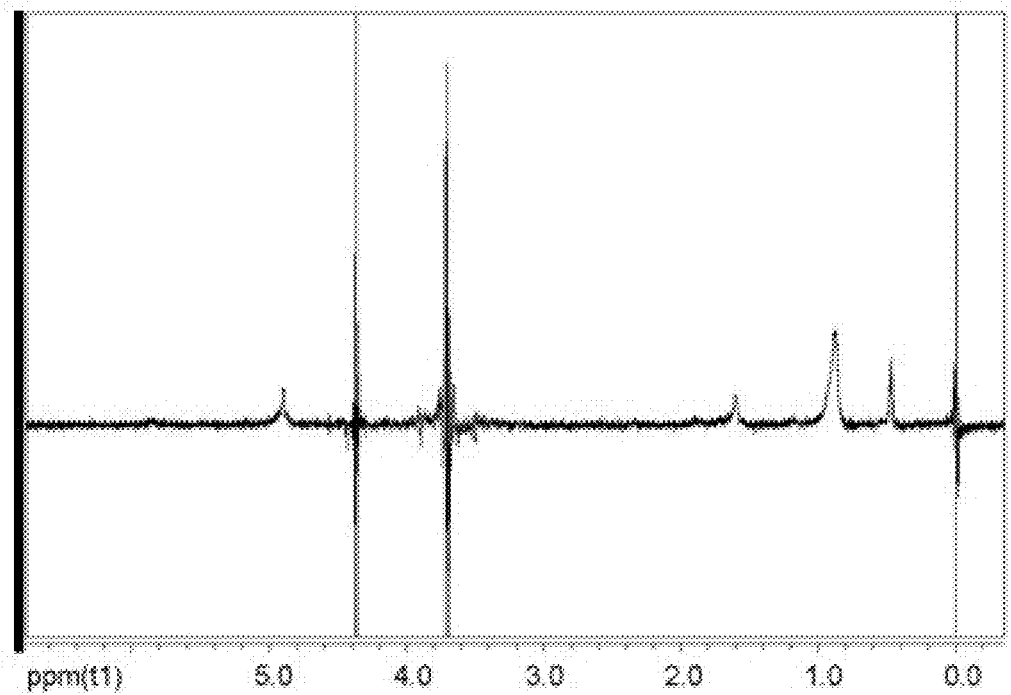
FIG. 21. 1D STD spectrum (STDoff-STDon difference) with selective saturation at 5.55 ppm for formulations NP80 (top image) and NP80OA (bottom image).
Figure 21:
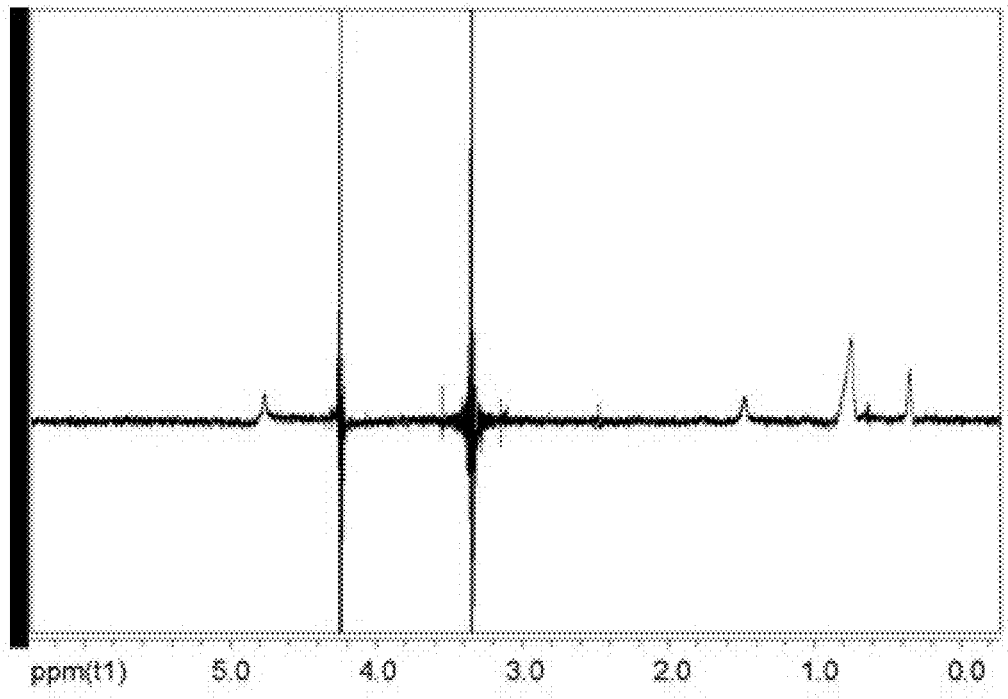

This result was obtained when repeating the STD experiment by saturating in another different area, which is also empty, of the spectrum at 5.5 ppm (FIG. 21).

This thus rules out the hypothesis referring to the existence of empty areas of the spectrum. In other words, said spectrum confirms that there are indeed protons corresponding to a molecule in that area of the spectrum. As a result, the only explanation for the existence of a proton spectrum having areas that are apparently empty but in which, however, the existence of protons is confirmed is that the signals are of an enormous width.

It must be taken into account that NMR is a quantitative technique, because the area of a signal is related with the number of protons. This means that the broader the signal, the shorter it is, but the area remains unchanged.

Figure 22:
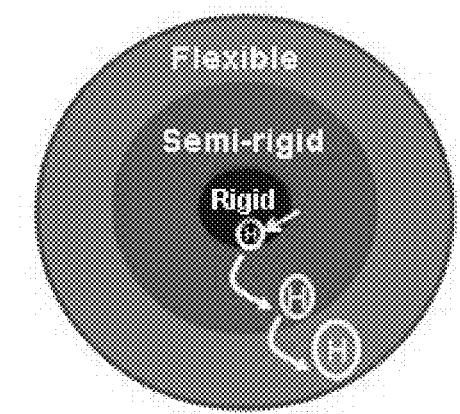
FIG. 22. Spherical nanoparticle model with a molecular flexibility gradient from the core (rigid) towards the outside (flexible).

In addition to the signals seen in the proton spectrum, there are other signals having signals that are too broad. This is because they are from the same molecules of the sample but are located in more rigid areas of the structure (supramolecular) (e.g. inside the particle) than the rest of signals seen in the spectrum located in more mobile areas (e.g. outside the particle), according to a structure such as that depicted in FIG. 22. The proton signals of the rigid interior can be extremely broad and not distinguishable from the level of noise of the "invisible" spectrum. The outermost areas of the particle have greater molecular flexibility and generate proton signals observable in the spectrum. In an STD experiment the saturation of "invisible" protons of the interior is very effectively transferred in several steps to the protons outside the particle. The effect can be seen in an STD spectrum because the proton signals appear in the most flexible areas of the nanoparticle. This model is according to that observed in the STD spectrum of FIG. 20.

The STD spectrum with saturation in the area without a signal at 0.12 ppm transfers any type of visible signals of the spectrum. This transfer can initially occur from apolar residues giving a signal at around 0.12 ppm and being transferred to the remaining visible signals of the molecule.

The STD spectrum with saturation in the area without a signal at 5.55 ppm preferably transfers to some visible signals, those which are closest to the C=C double bond in the molecule. This experiment is more interesting because it indicates that the apolar and polar areas of the molecules must be ordered in the macromolecular structure and spatially separated from the apolar areas. Otherwise the experiment would have given the same result as when saturation at 0.12 ppm is used. This would be in accordance with any of the structural models with polar and apolar chain ordering and aqueous interior or rigid interior. Other models with chains that are not ordered by polarity would be discarded.

Although the Waterlogsy spectrum is technically different from the STD spectrum, it can conceptually be considered an STD experiment in which saturation is performed in the signal of the solvent, $H_2O$.

Figure 23:
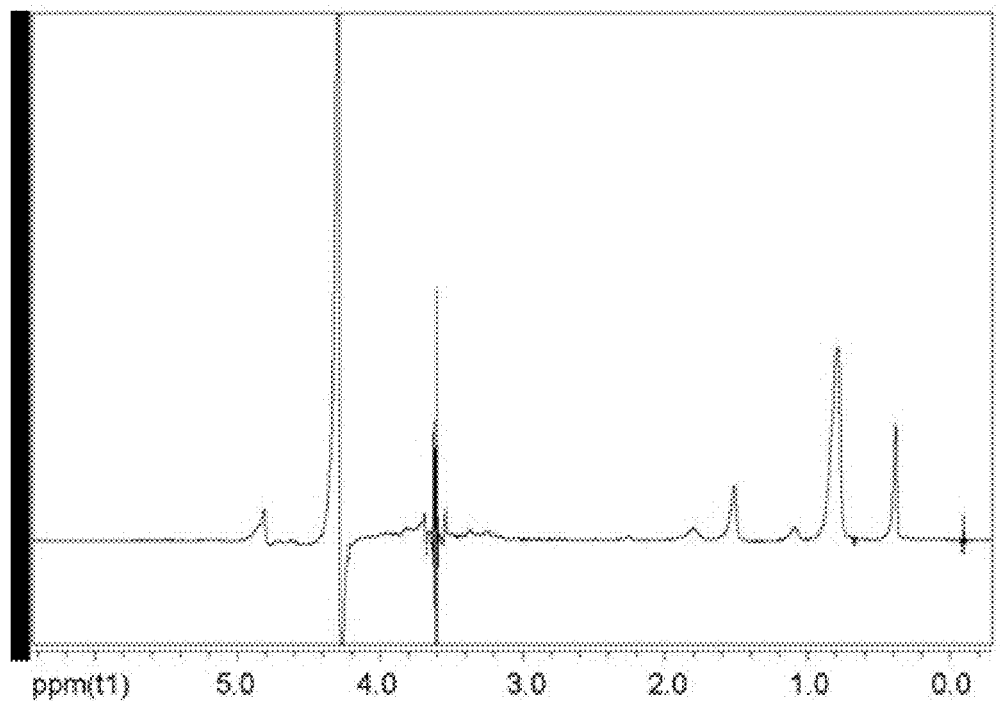
FIG. 23. Waterlogsy spectrum showing the signals for formulations NP80 (top image) and NP80OA (bottom image).
Figure 23:
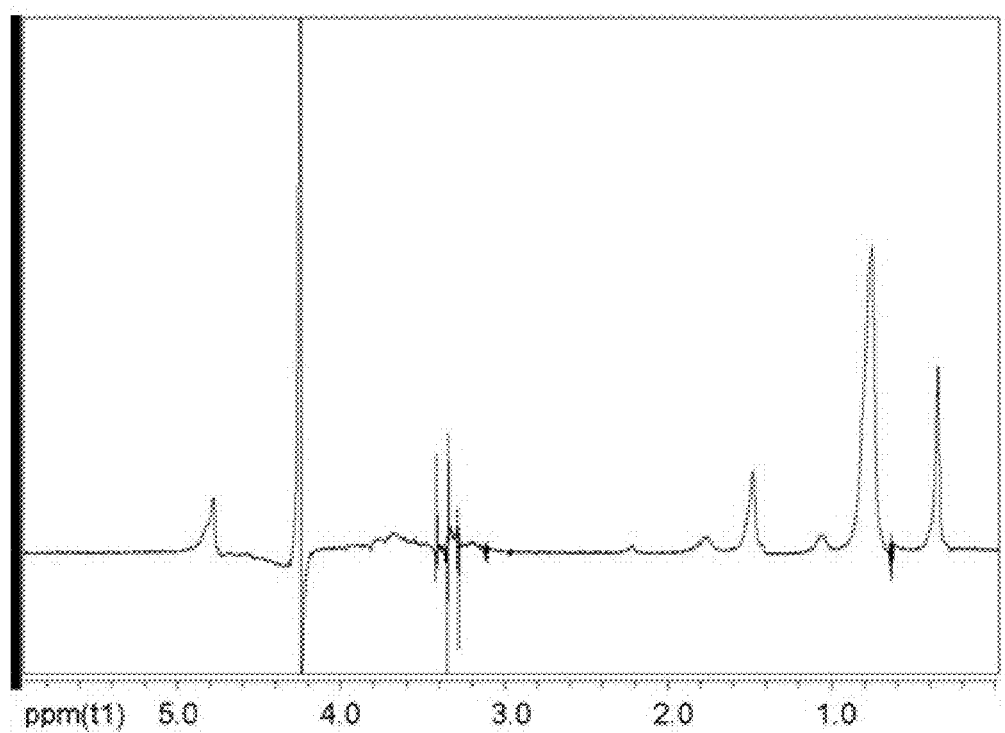

In the Waterlogsy spectra obtained for the NP80 and NP80OA samples shown in FIG. 23, $H_2O$ transfers any type of visible signals of the spectrum. This transfer can initially occur from the areas of the molecule exposed to $H_2O$ and be transferred to the rest of the visible signals of the molecule.

In conclusion and based on the obtained NMR results, the supramolecular structure possibilities that can be considered are, on one hand, a structure with polar and apolar chain ordering and an aqueous interior, i.e., which allows mobility for all the polymer chains (conventional micellar structure of a surfactant). In addition, it could be a solid structure with a rigid interior and without any solvent, formed by ordered polymer chains, i.e., with an increasing degree of rigidity from outside to inside (conventional matrix structure of a nanoparticle). The first model could take place taking into account the obtained STD and Waterlogsy spectra. However, there should not be areas with a great deal of rigidity, and therefore, said model is not in accordance with what is obtained in the diffusion spectrum (1H Dfilter). However, the second model or solid nanoparticulate system model would be in accordance with all the obtained spectra. It can therefore be concluded that the present invention relates to solid matrix nanoparticles consisting of Span® 80, which the difference of flexible structures in the form of single- or multilayer micelles, liposomes or niosomes such as those described in the literature for surfactants in general.

Example 17. Study of the Stability of the Lyophilized Nanoparticles Prepared Using Span® 80

The nanoparticulate system formed only using Span® 80 (NP80), as well as the systems described in Example 14, (NP80OA and 0.2 mg/ml NP80OA-pEGFP), were selected to subject them to a lyophilization process using 5% trehalose as the cryoprotective agent at a nanoparticle suspension: cryoprotectant solution ratio of 1:1 (volume/volume) and for the purpose of conducting a study of the stability over time. To that end, the stored lyophilized samples were subjected to different conditions, for example at 4° C. in a refrigerator, at room temperature (25° C.) and at 37° C. in a steaming cabinet. After 3 months the mean nanoparticle size and zeta potential were compared with those previously determined for the recently prepared, lyophilized and resuspended formulations (Lyophilized T=0). Tables 15, 16 and 17 show the results of said comparison. Said tables show that the analyzed size and zeta potential parameters barely experience significant modifications in the period of time studied. The formulations maintain their nanoparticulate size, detecting no aggregation phenomena, which allows concluding that the nanoparticulate systems prepared using Span® 80 with or without surface charge modifications by means of incorporating OA, and with or without the additional incorporation of an active ingredient, have good physical stability in storage in different conditions during the time the assay lasted, maintaining a nanometric size comprised between 116.3±5.2 and 279.1±30.5 nm in all the formulations.

TABLE 15

Size and surface charge of recently prepared, lyophilized and resuspended NP 80 nanoparticulate systems (Lyophilized T = 0) and of said lyophilized systems after 3 months of storage subjected to different conditions.

| | Lyophilized | Lyophilized and stored 3 months | | |
|---|---|---|---|---|
| NP80 | T = 0 | RT | 37° C. | 4° C. |
| Size (nm) | 157.6 ± 4.2 | 153.5 ± 3.3 | 158.1 ± 2.2 | 150.1 ± 3.5 |
| PDI | 0.136 | 0.122 | 0.149 | 0.132 |
| Zeta potential (mV) | −46.2 ± 2.1 | −35.3 ± 9.2 | −38.7 ± 8.9 | −40.1 ± 2.1 |

(RT: Room temperature)
(PDI = polydispersity index)

TABLE 16

Size and surface charge of recently prepared, lyophilized and resuspended NP 80OA nanoparticulate systems (Lyophilized T = 0) said and of lyophilized systems after 3 months of storage subjected to different conditions.

| | Lyophilized | Lyophilized and stored 3 months | | |
|---|---|---|---|---|
| NP80OA | T = 0 | RT | 37° C. | 4° C. |
| Size (nm) | 201.2 ± 4.8 | 211.1 ± 4.1 | 279.1 ± 30.5 | 206.8 ± 5.2 |
| PDI | 0.152 | 0.142 | 0.281 | 0.148 |
| Zeta potential (mV) | +46.7 ± 3.2 | +31.9 ± 3.4 | +11.5 ± 6.4 | +43.3 ± 7.1 |

(RT: Room temperature)
(PDI = polydispersity index)

TABLE 17

Size and surface charge of recently prepared, lyophilized and resuspended NP 80OA-pEGFP nanoparticulate systems (Lyophilized T = 0) and of said lyophilized systems after 3 months of storage subjected to different conditions.

| NP80OA-pEGFP | Lyophilized T = 0 | Lyophilized and stored 3 months | | |
|---|---|---|---|---|
| | | RT | 37° C. | 4° C. |
| Size (nm) | 250.1 ± 15.7 | 176.7 ± 7.2 | 192.5 ± 10.4 | 217.1 ± 12.4 |
| PDI | 0.301 | 0.209 | 0.371 | 0.179 |
| Zeta potential (mV) | −24.8 ± 2.9 | −17.1 ± 7.5 | −28.1 ± 9.9 | −20.3 ± 3.1 |

(RT: Room temperature)
(PDI = polydispersity index)

Figure 24:
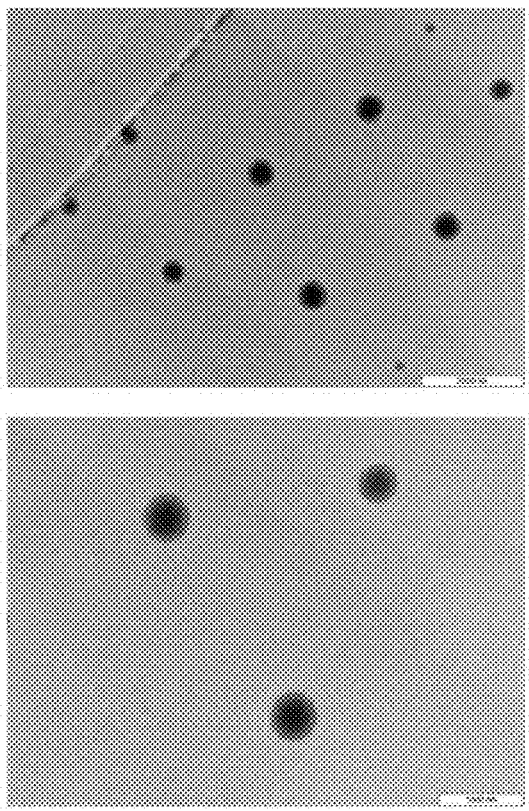
FIG. 24. Morphology of the lyophilized nanoparticles prepared using Span® 80 and OA (NP80OA) observed by means of transmission electron microscopy at different magnifications.

The lyophilized nanoparticulate systems were also observed by transmission electron microscopy to evaluate morphology. To that end, the lyophilized samples were included in EPON, and ultrafine cuts were subsequently made in an ultramicrotome (Leica UltraCut R) and they were observed under a microscope (TEM JEOL JEM-1011). By way of example, FIG. 24 shows the morphology of the lyophilized nanoparticles of NP80OA.

Figure 25:
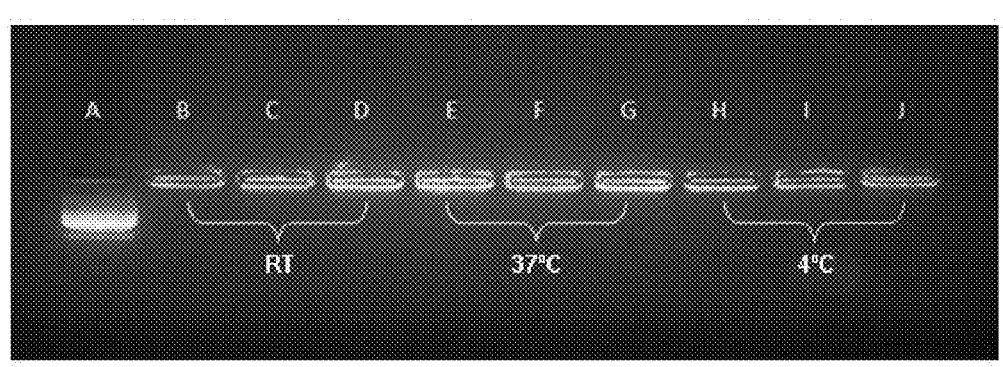
FIG. 25. Results of 1% agarose gel electrophoresis (100 V for 30 minutes). For the lyophilized nanoparticles associating plasmid DNA prepared using Span® 80 and OA (NP80OA-pEGFP 0.2 mg/ml), stored for 3 months and subsequently resuspended. (A) 0.2 mg/ml free pEGFP; (B, C, D) NP80OA-pEGFP stored at room temperature (RT); (E,F,G) NP80OA-pEGFP stored at 37° C.; (H,I,J) NP80OA-pEGFP stored at 4° C.

Then it was determined whether the suitable physical stability shown by the nanoparticles of the invention also allowed maintaining the association of the associated active molecule for the studied period. Specifically, the effective association of plasmid DNA with the lyophilized systems prepared using Span® 80 and with a surface charge modified by means of incorporating OA, (NP80OA-pEGFP) and stored for 3 months in different conditions and subsequently resuspended, can be confirmed by means of the agarose gel electrophoresis technique. FIG. 25 shows one of the gels obtained, in which bands due to the presence of plasmid can be observed. As can be seen, when the plasmid is deposited in free form, it migrates along the gel, giving rise to a characteristic band (A). In contrast, when the plasmid was associated with the nanoparticles and said systems were subjected to lyophilization, stored for three months in different conditions and resuspended, said band does not migrate and it remains in the output wells of the gel (B-J), confirming that the plasmid is not in free form, but rather effectively associated with the nanoparticulate systems deposited in the wells of said gel, which prevents plasmid migration. It can thereby be confirmed that after the lyophilization process, storage for 3 months in different conditions and subsequent resuspension, the nanoparticles continue to effectively associate with the model plasmid.

Example 18. Association of a Lipophilic Molecule with Nanoparticles Prepared Using Sorbitan Monooleate (Span® 80)

The nanoparticulate systems prepared using Span® 80 and with a positive surface charge due to the addition of OA (NP80OA) were used for associating a lipophilic molecule. To that end, rhodamine B was selected as the model lipophilic molecule.

For the preparation of the nanoparticles, an organic solution was prepared by dissolving the components Span® 80 (6.6 mg/ml), OA (0.33 mg/ml) and rhodamine B (0.16, 0.33, 1.66, 3.33, 6.66 microg/ml) in 30 ml of ethanol. This organic phase was added to an aqueous phase of 60 ml of Milli-Q water subjected to magnetic stirring, causing spontaneous nanoparticle formation. Then ethanol was removed in a rotavapor and the volume of the nanoparticle suspension was concentrated to a final volume of 10 ml. In that volume the final theoretical rhodamine B concentration in the studied formulations is 0.5, 1, 5, 10 and 20 microg/ml.

Rhodamine B association efficiency was calculated indirectly from the free molecule recovered in the residual medium obtained after separating the nanoparticles by means of centrifugation (14000 rpm, 3.5 h, 4° C.). The amount of free rhodamine B was determined using the quantitative UV spectroscopy technique at a wavelength of 554 nm. The results of the association efficiency of the lipophilic molecule with the nanosystems are shown in Table 18.

TABLE 18

Association efficiency of the lipophilic rhodamine B molecule with the nanoparticles prepared using sorbitan monooleate (Span® 80) and with a surface charge modulated by means of incorporating OA (NP80OA).

| Rhodamine B (microg/ml) | Size (nm) | PDI | % of Association |
|---|---|---|---|
| 0.5 | 213.7 ± 3.2 | 0.087 | 99.9 ± 2.5 |
| 1 | 191.1 ± 3.4 | 0.096 | 88.1 ± 10.5 |
| 5 | 192.2 ± 3.1 | 0.092 | 82.1 ± 3.7 |
| 10 | 181.9 ± 4.6 | 0.093 | 81.9 ± 7.8 |
| 20 | 165.8 ± 7.2 | 0.073 | 79.2 ± 3.7 |

(PDI: Polydispersity index)

As can be seen, the nanoparticles of the invention effectively associate with a lipophilic molecule.

The invention claimed is:

1. A nanoparticle comprising a sorbitan ester in a proportion by weight of between 60% and 100%, of the nanoparticle characterized by being a solid homogenous matrix formed using an organic phase comprising the sorbitan ester and a solvent, wherein the solvent of the organic phase is a water-miscible solvent, selected from aliphatic alcohols the mean size of which is comprised between 1 and 999 nm, wherein the ester group has a substituent selected from $C_6$-$C_{24}$ alkyl, $C_6$-$C_{24}$ alkenyl and $C_6$-$C_{24}$ alkynyl.

2. The nanoparticle according to claim 1, where the sorbitan ester is selected from the group consisting of sorbitan mono-, di-, tri- or sesquioleate; sorbitan mono-, di-, tri- or sesquilaurate; sorbitan mono-, di-, tri- or sesquipalmitate; sorbitan mono-, di-, tri- or sesquistearate; and sorbitan mono-, di-, tri- or sesquiisostearate; and their combinations.

3. The nanoparticle according to claim 1, further comprising a cationic substance, an anionic substance, an ethylene oxide derivative, or combinations thereof.

4. The nanoparticle according to claim 3, where the cationic substance is selected from ammonium salts, cationic polymers and fatty amines.

5. The nanoparticle according to claim 4, where the cationic polymer is selected from protamine, polyglutamic acid, cationized dextran, polyamino acids and cationized proteins, and their salts.

6. The nanoparticle according to claim 3, where the anionic substance is an anionic polymer selected from the group consisting of hyaluronic acid, colominic acid, polysialic acid, chondroitin, keratan, dextrans, heparin, carrageenans, furcellarans, alginates, agar-agar, glucomannan, gellan gum, locust bean gum, guar gum, tragacanth gum, acacia gum, xanthan gum, karaya gum, pectins, celluloses, starches, their salts, fragments, derivatives or combinations thereof.

7. The nanoparticle according to claim 3, where the ethylene oxide derivative is selected from polyethylene glycol dodecyl ether (Brij 30), polyethylene glycol hexadecyl ether (Brij 56), polyethylene glycol 2-octadecyl ether (Brij 72), polyethylene glycol 8-octadecyl ether (Brij 78), polyethylene glycol 8-stearate (Myrj 45), 2-hydroxyethyl octadecanoate (Myrj 52), ethylene glycol monostearate, triethylene glycol monostearate.

8. The nanoparticle according to claim 1, further comprising an active ingredient.

9. The nanoparticle according to claim 1, further comprising a compound selected from a marker, an adjuvant, an immunomodulator, an antibody, an aptamer, a surface receptor, a stabilizing compound, a compound susceptible to chemical polymerization or combinations thereof.

10. The nanoparticle according to claim 1, which is in lyophilized form.

11. A pharmaceutical composition comprising a nanoparticle as described in claim 1, and a pharmaceutically acceptable carrier.

12. A cosmetic composition comprising a nanoparticle as described in claim 1.

13. A nutritional composition comprising a nanoparticle as described in claim 1.

14. A medical device comprising a nanoparticle as described in claim 1.

15. A method for the preparation of a nanoparticle as described in claim 1, comprising the following steps:
  a) preparing an organic phase comprising a sorbitan ester and a solvent, wherein the sorbitan ester is present in a proportion by weight of between 60% and 100%, of the nanoparticle wherein the ester group has a substituent selected from $C_6$-$C_{24}$ alkyl, $C_6$-$C_{24}$ alkenyl and $C_6$-$C_{24}$ alkynyl;
  b) mixing under stirring the solution obtained in a) with an aqueous solution wherein injection is not used, thereby forming a dispersion of the nanoparticles; wherein the solvent of the organic phase is a water-miscible solvent selected from aliphatic alcohols.

16. The method according to claim 15, where the organic phase of step a) and/or the aqueous solution of step b) furthermore comprises a cationic substance, an anionic substance or both.

17. The method according to claim 15, further comprising a step c) which comprises incubating the dispersion of nanoparticles formed in step b) with a solution comprising a cationic substance, an anionic polymer or a combination of both.

18. The method according to claim 15, where the organic phase of step a) further comprises an ethylene oxide derivative.

19. The method according to claim 15, further comprising the addition of an active ingredient, and/or a compound selected from a marker, an adjuvant, an immunomodulator, an antibody, an aptamer, a surface receptor, a stabilizing compound, a compound susceptible to chemical polymerization or combinations thereof, in one of solutions a) or b) depending on the lipophilic or hydrophilic nature thereof.

20. The method according to claim 15, further comprising the addition of an active ingredient, and/or a compound selected from a marker, an adjuvant, an immunomodulator, an antibody, an aptamer, a surface receptor, a stabilizing compound, a compound susceptible to chemical polymerization or combinations thereof, in a step c) after step b).

21. The method according to claim 15, comprising an additional step after step b) in which the dispersion of nanoparticles formed in step b) is subjected to a complete or partial dehydration process or lyophilization.

22. The method according to claim 21, comprising an additional step in which the partially dehydrated or lyophilized nanoparticles are regenerated.

* * * * *

UNITED STATES PATENT AND TRADEMARK OFFICE
CERTIFICATE OF CORRECTION

PATENT NO. : 9,861,588 B2  
APPLICATION NO. : 14/357211  
DATED : January 9, 2018  
INVENTOR(S) : Alejandro Sanchez Barreiro et al.

It is certified that error appears in the above-identified patent and that said Letters Patent is hereby corrected as shown below:

In the Specification

Column 3, Line 35: "R. H. Advanced Drug Delivery" should be --R.H. Müller, Advanced Drug Delivery--.

Column 33, Line 64: "stimulated with 4=350 ms, 5=1 ms and" should be --stimulated with $\Delta$=350 ms, $\delta$=1 ms and--.

Column 34, Line 28: "neither isolated nor not in solution" should be --neither isolated nor in solution--.

Signed and Sealed this  
Twenty-second Day of May, 2018

Andrei Iancu  
*Director of the United States Patent and Trademark Office*